United States Patent
Li et al.

(10) Patent No.: US 11,667,674 B2
(45) Date of Patent: *Jun. 6, 2023

(54) ANTIBACTERIAL CYCLIC LIPOPEPTIDES

(71) Applicant: Versitech Limited, Hong Kong (HK)

(72) Inventors: Xuechen Li, Hong Kong (HK); Hoi Yee Chow, Kowloon (HK)

(73) Assignee: VERSITECH LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/310,364

(22) PCT Filed: Mar. 24, 2017

(86) PCT No.: PCT/CN2017/078056
§ 371 (c)(1),
(2) Date: Dec. 14, 2018

(87) PCT Pub. No.: WO2017/173932
PCT Pub. Date: Oct. 12, 2017

(65) Prior Publication Data
US 2020/0010506 A1    Jan. 9, 2020

Related U.S. Application Data

(63) Continuation-in-part of application No. 15/093,950, filed on Apr. 8, 2016, now Pat. No. 10,647,746.
(Continued)

(51) Int. Cl.
*C07K 7/08* (2006.01)
*A61P 31/04* (2006.01)
*A61K 38/00* (2006.01)

(52) U.S. Cl.
CPC ............ *C07K 7/08* (2013.01); *A61P 31/04* (2018.01); *A61K 38/00* (2013.01)

(58) Field of Classification Search
CPC ............ A61K 38/00; C07K 7/08; C07K 7/54; C07K 11/02; C07K 7/56; A61P 31/04
See application file for complete search history.

(56) References Cited

U.S. PATENT DOCUMENTS 4,482,487 A * 11/1984 Abbott .................... C07K 7/08
530/317
4,537,717 A    8/1985 Lilly
(Continued)

FOREIGN PATENT DOCUMENTS

GB        2120257        11/1983
WO     1999/043700      9/1999
(Continued)

OTHER PUBLICATIONS

Hill et al., Synthesis and Biological Activity of N-acylated Ornithine Analogues of Daptomycin, Bioorganic & Medicinal Chemistry Letters, 13:4187-4197 (2003). (Year: 2003).*
(Continued)

*Primary Examiner* — Randall L Beane
(74) *Attorney, Agent, or Firm* — Pabst Patent Group LLP

(57) ABSTRACT

Cyclic lipopeptides having one or more modifications relative to daptomycin, and methods of making them are provided. The cyclic lipopeptides can be used as antibacterial agents. The daptomycin analogues are generated by chemical synthesis, which makes introduction of an unnatural amino acid and any modification into daptomycin possible. Pharmaceutical compositions and method of use thereof for the disclosed daptomycin analogues are also provided.

8 Claims, 5 Drawing Sheets

Daptomycin

Related U.S. Application Data

(60) Provisional application No. 62/438,138, filed on Dec. 22, 2016.

(56) References Cited

U.S. PATENT DOCUMENTS

| | | | | |
|---|---|---|---|---|
| 5,912,226 | A * | 6/1999 | Baker | C07K 7/08 514/2.4 |
| 6,468,967 | B1 | 10/2002 | Oleson | |
| 6,624,143 | B1 | 9/2003 | Vertesy | |
| 6,852,689 | B2 | 2/2005 | Oleson | |
| RE39,071 | E | 4/2006 | Baker | |
| 8,058,238 | B2 | 11/2011 | Kelleher | |
| 8,129,342 | B2 | 3/2012 | Kelleher | |
| 8,507,647 | B2 | 8/2013 | Metcalf | |
| 8,754,040 | B2 | 6/2014 | Sekimizu | |
| 8,835,382 | B2 | 9/2014 | O'Connor | |
| 8,853,357 | B2 | 10/2014 | Kelleher | |
| 9,090,667 | B2 | 7/2015 | Kim | |
| 9,138,456 | B2 | 9/2015 | O'Connor | |
| 9,243,036 | B2 | 1/2016 | Atreya | |
| 9,260,481 | B2 | 2/2016 | Gualtieri | |
| 9,283,287 | B2 | 3/2016 | Chakraborty | |
| 9,303,079 | B2 | 4/2016 | Chakraborty | |
| 10,377,699 | B2 * | 8/2019 | Li | C07K 7/08 |
| 10,647,746 | B2 * | 5/2020 | Li | C07K 7/08 |
| 2003/0224475 | A1 * | 12/2003 | Leese | C07K 11/02 435/68.1 |
| 2010/0184649 | A1 * | 7/2010 | MetCalf, III | A61P 37/04 530/323 |
| 2015/0126707 | A1 | 5/2015 | Li | |
| 2017/0291923 | A1 | 10/2017 | Li | |

FOREIGN PATENT DOCUMENTS

| | | | | |
|---|---|---|---|---|
| WO | 01/44274 | | 6/2001 | |
| WO | WO-0144274 | A1 * | 6/2001 | C07K 7/08 |
| WO | 2002/005837 | | 1/2002 | |
| WO | 2002/056829 | | 7/2002 | |
| WO | WO-03014147 | A1 * | 2/2003 | C07K 7/08 |
| WO | 2007/072082 | | 6/2007 | |
| WO | WO-2010075215 | A1 * | 7/2010 | C07K 7/54 |
| WO | 2012/162567 | | 11/2012 | |
| WO | WO-2015172047 | A1 * | 11/2015 | A61K 38/00 |

OTHER PUBLICATIONS

Lam et al., Total Synthesis of Daptomycin by Cyclization via a Chemoselective Serine Ligation, J. Am. Chem. Soc., vol. 135:6272-6279 (Apr. 5, 2013). (Year: 2013).*

Baltz et al., Natural products to drugs: daptomycin and related lipopeptide antibiotics, Nat. Prod. Rep., vol. 22:717-741 (2005) (Year: 2005).*

He et al., Reduced pulmonary surfactant interaction ofdaptomycin analogs via tryptophan replacement with alternative amino acids, Bioorganic & Medicinal Chemistry Letters, vol. 22:6248-6251 (Aug. 9, 2012) (Year: 2012).*

Baltz et al., Combinatorial biosynthesis of lipopeptide antibiotics in *Streptomyces roseosporus*, J. Ind. Microbiol. Biotechnol., vol. 33:66-74 (2006) (Year: 2006).*

Muangsiri et al., The protein-binding and drug release properties of macromolecular conjugates containing daptomycin and dextran, International Journal of Pharmaceutics, vol. 315: 30-43 (Mar. 2006) (Year: 2006).*

Lohani et al., α-Azido Acids in Solid-Phase Peptide Synthesis: Compatibility with Fmoc Chemistry and an Alternative Approach to the Solid Phase Synthesis of Daptomycin Analogs, J. Org. Chem., vol. 81:2624-2628 (Mar. 3, 2016) (Year: 2016).*

Robbel et al., Daptomycin, a Bacterial Lipopeptide Synthesized by a Nonribosomal Machinery, J. of Biol. Chem., vol. 285(36):27501-27508 (Sep. 3, 2010) (Year: 2010).*

Li., Long Journey on Daptomycin, Synlett, vol. 33:27-33 (online Oct. 26, 2021) (Year: 2021).*

Cucherat, et al., Summary Report: Indirect comparisons Methods and valididty, *HAS Department of Medecines Assessment*, (2009).

Fox, et al., "Transdermal Drug Delivery Enhancement by Compounds of Natural Origin", *Molecules*, 16:10507-10540 (2011).

Inayat, et al., "Chemical Penetration Enhancers for Transdermal Drug Delivery Systems", *Tropical Journal of Pharmaceutical Research*, 8(2):173-179 (2009).

Li, et al., "Preparation and characterization of flexible nanoliposomes loaded with daptomycin, a novel antibiotic, for topical skin therapy", *Int. J Nanomedicine*, 8:1285-1292 (2013).

Mathiowitz et al., "Novel microcapsules for delivery systems", *Reactive Polymers*, 6(2-3):275-283 (1987).

Mathiowitz, et al., "Polyanhydride microspheres as drug carriers I. Hot-melt microencapsulation", *J Controlled Release*, 5:13-22 (1987).

Mathiowitz et al., "Polyanhydride microspheres as drug carriers II. Microencapsulation by solvent removal", *J. Appl. Polymer Sci.*, 35:755-774 (1988).

Mengeloglu, et al., "Efficacy of daptomycin on experimental methicillin-resistant *Staphylococcus aureus* keratitis in rabbits", *J Ocul. Pharmacol. Ther.*, 29(10):893-899 (2013).

Mills, et al., Estimating the Power of Indirect Comparisons: A Simulation Study. PLoS One 6(1):e16237 (2011).

Muangsiri, et al., Studies on the reactions between daptomycin and glyceraldehyde, *International Journal of Pharmaceutics*, 289:133-150 (2005).

Song, et al., Validity of indirect comparison for estimating efficacy of competing interventions: empirical evidence from published meta-analyses, BMJ, vol. 326:1-5 (2003).

International Search Report PCT/CN2017/078056 dated May 31, 2017.

* cited by examiner

Daptomycin

Modification 1 (methylation at Gly)

Modification 2 (methylation at Kyn)

Modification 3 (methylation at Trp)

Modification 4 (methylation at Orn)

Modifications 5 (at the lipid)

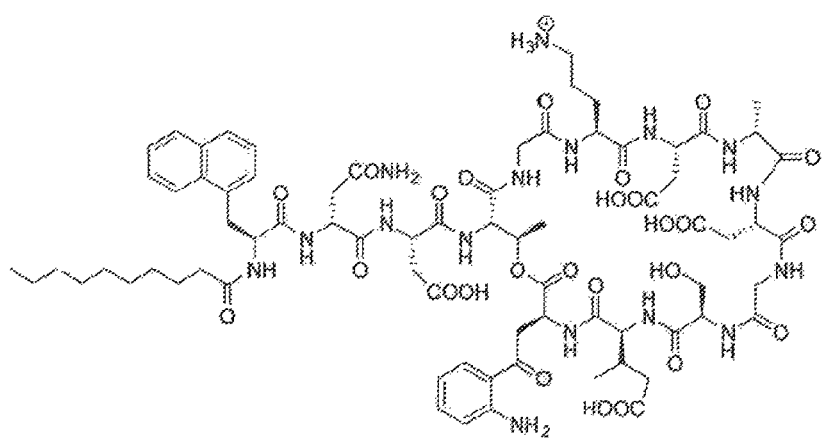
Modification 6
Fig. 7
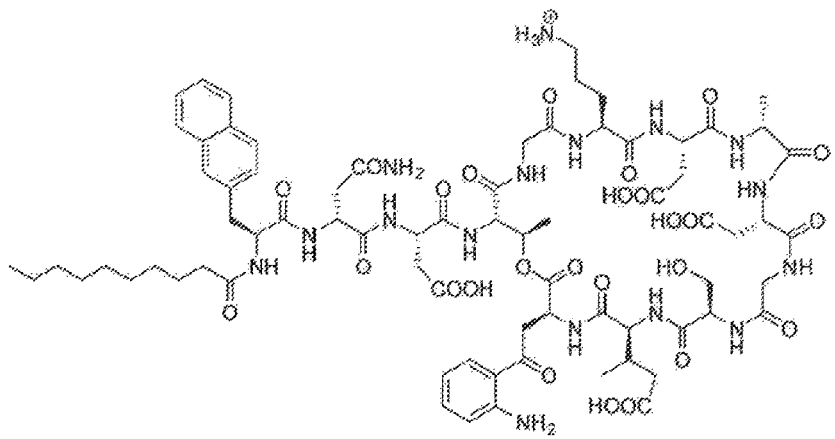

ANTIBACTERIAL CYCLIC LIPOPEPTIDES

CROSS-REFERENCE TO RELATED APPLICATIONS

This application is a National Phase application under 35 U.S.C. 371 of PCT/CN2017/078056, filed in the Intellectual Property Office of the People's Republic of China receiving office for the PCT on Mar. 24, 2017, which is a continuation-in-part of U.S. Utility application Ser. No. 15/093,950, filed Apr. 8, 2016, and claims benefit of and priority to U.S. Provisional Application No. 62/438,138, filed Dec. 22, 2016, and where permissible each of which are specifically incorporated by reference in their entireties.

FIELD OF THE INVENTION

The invention is in the field of antibacterial agents, particularly antibacterial cyclic lipopeptides.

BACKGROUND OF THE INVENTION

Despite the current availability of antibacterial agents, the need for improved antibiotics continues. One of the reasons is that antibiotics differ in their effectiveness against different pathogenic organisms. Further, pathogenic organisms are known to develop resistance to antibiotics that were once effective against the organisms. Exacerbating this situation is that individual patients frequently suffer serious reactions to specific antibiotics, due to hypersensitivity and/or to toxic effects. Consequently, there is a continuing need for new and improved antibiotics.

Many cyclic peptides have potent antibacterial activities. For instance, daptomycin is a cyclic lipodepsipeptide consisting of 13 amino acids, 10 of which make up a 31-membered ring and three are anchored as an exocyclic tail with the N-terminal containing n-decanoyl lipid. Within this structure are two unnatural amino acids, kynurenine (Kyn) and 3-methyl-glutamic acid (3-mGlu), as well as three D amino acids (i.e., D-Asn, D-Ala and D-Ser). Functionally, this compound exhibits a unique mode of action which is significantly different from that of other currently used antibiotics: it first undergoes a conformational change upon binding to $Ca^{2+}$ ions, so that the entire structure can be inserted into bacterial membranes via the lipid tail, which then induces membrane leakage and cell death.

Efforts have previously been made by various research groups to establish the structure-activity relationship (SAR) of daptomycin and to produce its analogues. However, since daptomycin can only be produced by fermentation, only a limited number of daptomycin analogues with few structural variations can be generated via genetic engineering of the non-ribosomal peptide synthetase in the daptomycin biosynthetic pathway, and by chemoenzymatic and semisynthesis approaches. These analogues are limited to swapping natural amino acids. None of these daptomycin analogues have shown better antibacterial activities than the parent daptomycin. Indeed, these above-mentioned approaches cannot generate analogues containing modifications at position Trp1, Thr4, Gly5, Orn6, and Kyn13 of daptomycin, and cannot substitute the residues of daptomycin with unnatural amino acids.

Therefore, it is an object of the present invention to provide analogues of daptomycin.

It is also an object of the present invention to provide analogues of daptomycin, which contain modifications at Trp1, Thr4, Gly5, Orn6, Kyn13, and combinations thereof.

It is also an object of the present invention to provide analogues of daptomycin, which contain unnatural amino acids.

It is a further object of the present invention to provide a method of making analogues of daptomycin, which contain modifications at Trp1, Thr4, Gly5, Orn6, Kyn13, and combinations thereof.

It is also an object of the invention to provide methods of using the disclosed compounds, particularly as antimicrobial agents.

SUMMARY OF THE INVENTION

Described herein are a set of cyclic lipopeptides based on modifications of daptomycin, their methods of making and using. The cyclic lipopeptides can be used as antibacterial agents.

The cyclic lipopeptides have the general formula:

(I)

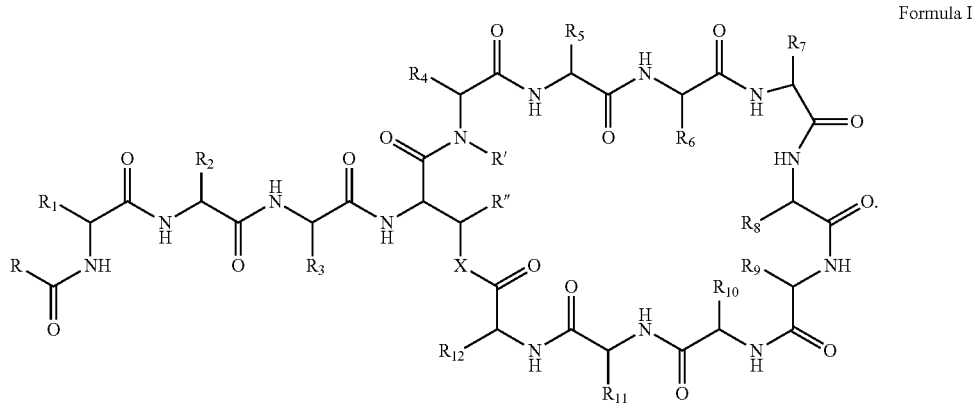

Formula I

Preferably, when present, R is substituted aryl or substituted alkenyl; R5 is —$(CH_2)_x$—$NR^*_2$, x is three and each R* is independently unsubstituted alkyl, substituted alkyl, substituted aryl, or unsubstituted aryl, preferably are both unsubstituted alkyl (e.g. methyl); R1 is substituted polyheteroaralkyl (e.g. N-alkylated indol-3-ylalkyl such as N-methyl indol-3-ylmethyl), unsubstituted polyaralkyl (e.g.

1-naphthylalkyl and 2-naphthylalkyl such as 1-naphthylmethyl and 2-naphthylmethyl, respectively); R' is hydrogen, unsubstituted alkyl (e.g. methyl), substituted alkyl, unsubstituted aryl, or unsubstituted aryl; R" is hydrogen, unsubstituted alkyl (e.g. methyl and ethyl), substituted alkyl, unsubstituted aryl, or unsubstituted aryl; and R12 is a substituted alkyl containing a substituted aniline; and X is O or NH.

The cyclic lipopeptides are generated, preferably, by chemical synthesis, which facilitates the introduction of an unnatural amino acid or modification into daptomycin. Chemical synthesis was used to generate analogues with wider modifications and to introduce modifications at Trp1, Thr4, Gly5, and Kyn13. In some forms, these generated cyclic lipopeptides have N-alkylated or N-acylated kynurenine to replace kynurenine (Kyn13); N-alkyl indol-3-ylalkyl (N-methyl indol-3-ylmethyl, i.e., MeTrp), 1-naphthylmethyl, or 2-naphthylmethyl to replace Trp1; sarcosine to replace Gly5, an alkylated Orn to replace Orn6; and/or 2,3-diaminobutyric acid or 2,3-diaminopropionic acid to replace Thr4.

Pharmaceutical compositions including the disclosed compounds and methods of use thereof for treating subject in need thereof are also provided.

BRIEF DESCRIPTION OF THE DRAWINGS

FIG. 7 illustrates two chemical structures of replacing Trp1 with 1-naphthylmethyl or 2-naphthylmethyl within daptomycin.

DETAILED DESCRIPTION OF THE INVENTION

I. Definitions

Figure 1:
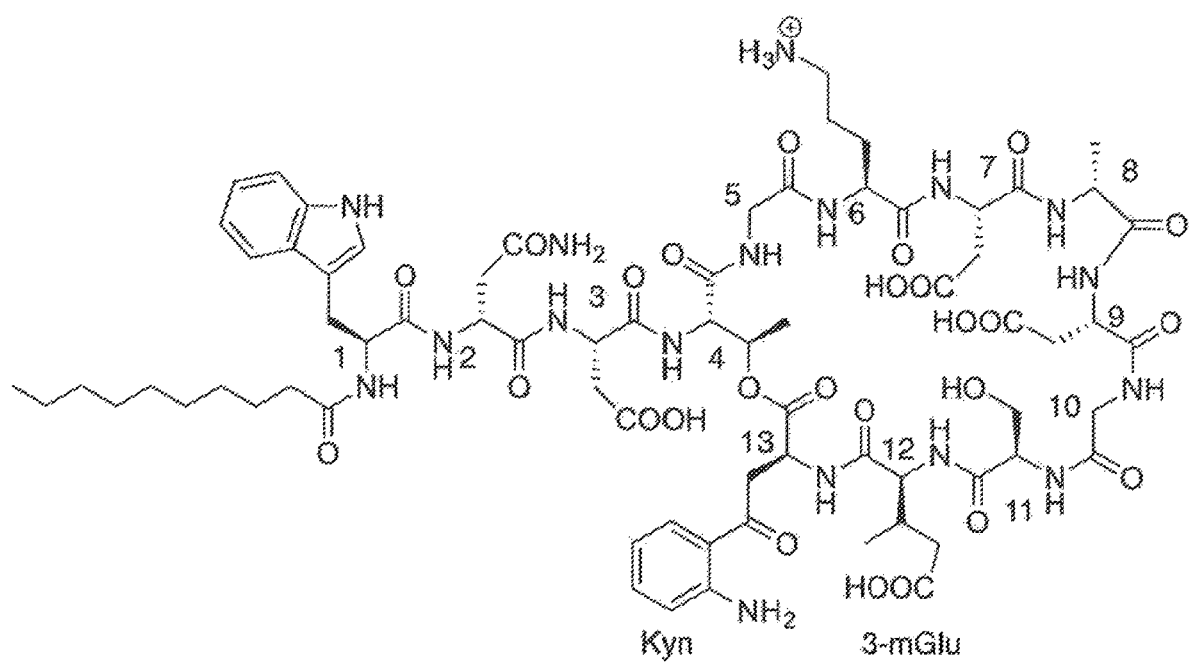
FIG. 1 illustrates the chemical structure of daptomycin with amino acid numbering.
Figures 2, 3:
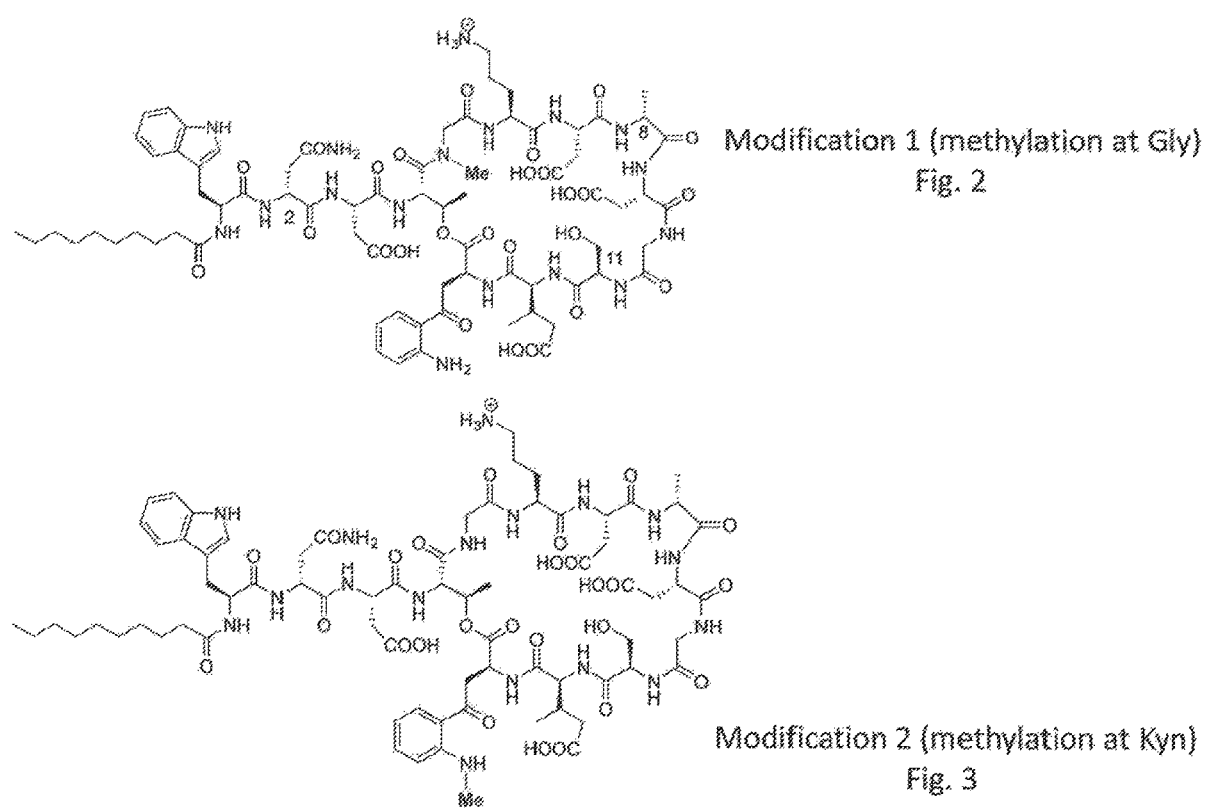
FIG. 2 illustrates the chemical structure of methylation at Gly5 within daptomycin.
FIG. 3 illustrates the chemical structure of methylation at Kyn13 within daptomycin.
Figure 4:
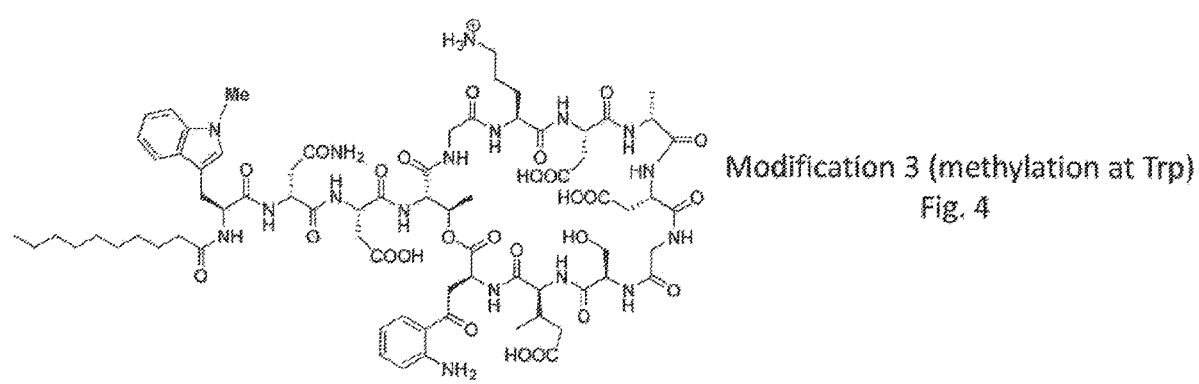
FIG. 4 illustrates the chemical structure of methylation at Trp1 within daptomycin.
Figure 5:
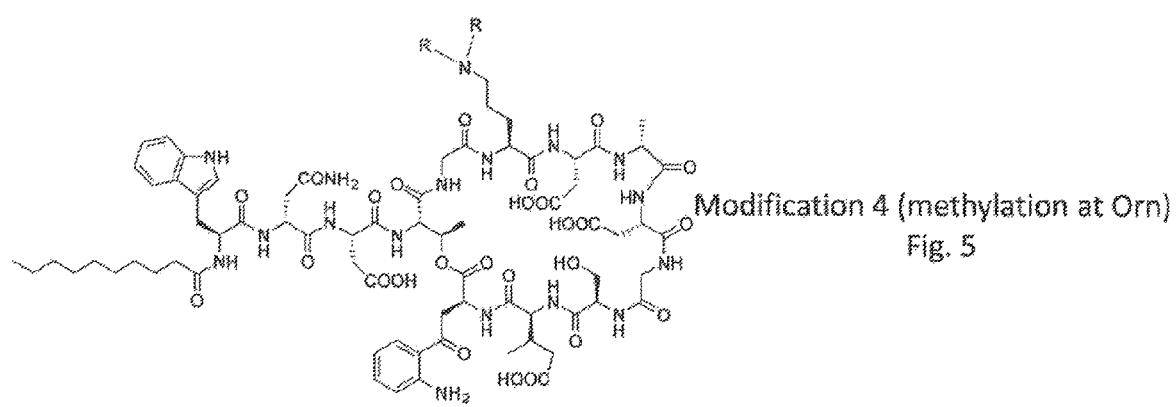
FIG. 5 illustrates the chemical structure of methylation at Orn5 within daptomycin.
Figure 6:
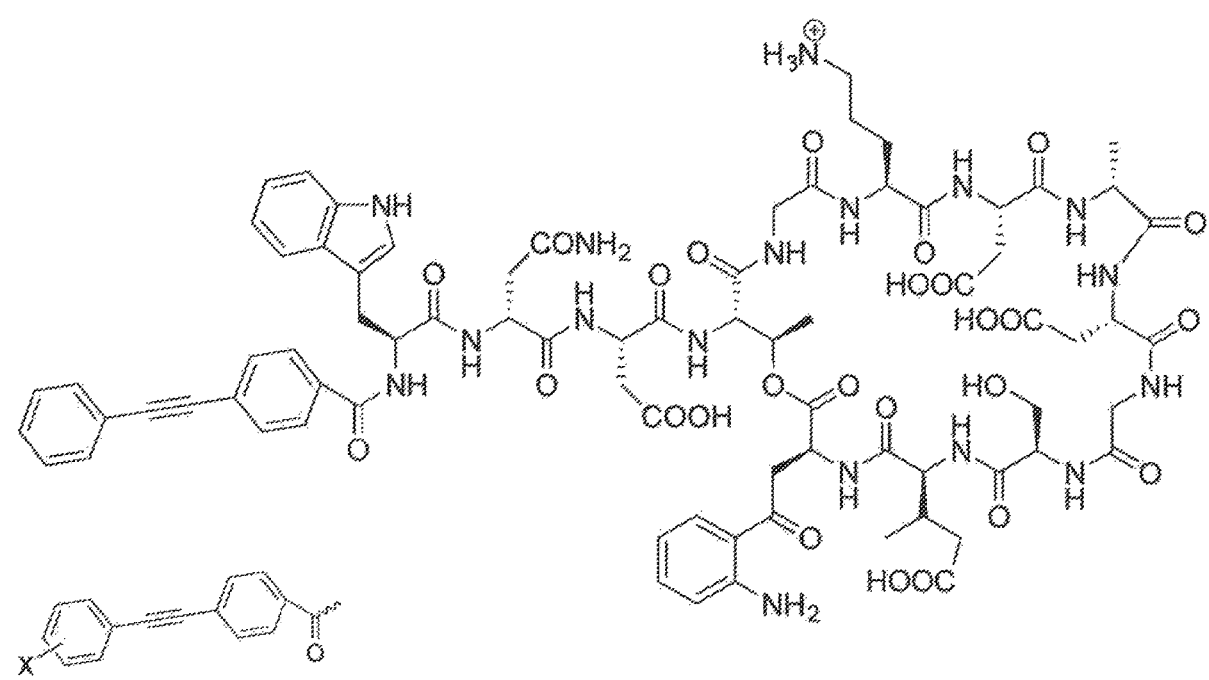
FIG. 6 illustrates the chemical structure of acylation at the lipid within daptomycin, and an alternative structure for the acylating group.

To facilitate the understanding of the subject matter disclosed herein, a number of terms, abbreviations or other shorthand as used herein are defined below. Unless otherwise defined, all technical and scientific terms used herein have the meaning as commonly understood by one of ordinary skill in the art to which this invention belongs. The practice of the invention employs, unless otherwise indicated, conventional techniques of chemistry, biochemistry and microbiology and basic terminology used therein.

It is to be understood that the disclosed compounds, compositions, and methods are not limited to specific synthetic methods, specific analytical techniques, or to particular reagents unless otherwise specified, and, as such, may vary. It is also to be understood that the terminology used herein is for the purpose of describing particular forms and embodiments only and is not intended to be limiting.

The term "amino acid" as used herein refers to a molecule containing both an amino group and a carboxyl group. Amino acids include alpha-amino acids and beta-amino acids. In certain forms, an amino acid is an alpha amino acid. Amino acids can be natural or synthetic. Amino acids include, but are not limited to, the twenty standard or canonical amino acids: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Common non-standard or non-canonical amino acids include, but are not limited to, selenocysteine, pyrrolysine, and N-formylmethionine.

The term "natural amino acid" as used herein refers to both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)).

The terms "synthetic amino acid," "non-natural amino acid," and "unnatural amino acid," are used interchangeably, and refer to an organic compound that has an amino group and a carboxyl group, and is not one of the D- and L-isomers of the 20 common naturally occurring amino acids found in peptides. Generally, it mimics the reactivity of a natural amino acid due to the presence of the amino and carboxyl groups. "Synthetic amino acid," "non-natural amino acid," or "unnatural amino acid" also refers to an amino acid that is not produced by an organism without genetic engineering. The synthetic amino acid as defined herein generally increases or enhances the properties of a peptide (e.g., selectivity, stability) when the synthetic amino acid is either substituted for a natural amino acid or incorporated into a peptide. Non-limiting examples include N-methyl kynurenine, N,N-dimethyl kynurenine, N-methyl ornithine, N,N-dimethyl ornithine, N-methyl glycine (sarcosine), 2,3-diaminobutyric acid, 2,3-diamino propionic acid, and alpha-amino acids with the following side chains: 1-naphthylmethyl, 1-naphthylmethyl, and N-methyl indol-3-ylmethyl.

The term "isolated" refers to a compound or product that is refers to a compound which represents at least 10% by wt, at least 20% by wt, at least 30%, at least 50% by wt, at least 60% by wt, at least 70% by wt, at least 80% by wt, at least 90% by wt, or at least 95% by wt of the compound present in the mixture.

The term "lipopeptide" refers to a molecule that comprises a lipid-like moiety covalently linked to a peptide moiety, as well as salts, esters, amides and ethers thereof. The term "lipopeptide" also encompasses protected forms of lipopeptides in which one or more amino, carboxylate or hydroxyl groups are protected.

"Amino" and "Amine," as used herein, are art-recognized and refer to a primary, secondary, or tertiary amine which may be optionally substituted, e.g. a moiety that can be represented by the general formula:

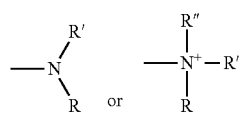

wherein, R, R', and R" each independently represent a hydrogen, substituted or unsubstituted alkyl, substituted or unsubstituted alkenyl, substituted or unsubstituted alkynyl, substituted or unsubstituted carbonyl, —(CH$_2$)$_m$—R'", or R and R' taken together with the N atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —(CH$_2$)$_m$—R'". Thus, the term 'alkylamine' as used herein refers to an amine group, as defined above, having a substituted alkyl or unsubstituted alkyl attached thereto (i.e. at least one of R, R', or R" is an alkyl group). The term "dialkylamine" refers to an amine group, as defined above, having two substituted alkyl or unsubstituted alkyl attached thereto. Specifically included are secondary or tertiary amine nitrogen atoms which are members of a heterocyclic ring. Also specifically included, are secondary or tertiary amino groups substituted by an acyl moiety. Some non-limiting examples of an amino group include —NR'R" wherein each of R' and R" is independently H, alkyl, aryl, aralkyl, alkaryl, cycloalkyl, acyl, heteroalkyl, heteroaryl or heterocycyl.

"Alkyl," as used herein, refers to the radical of saturated aliphatic groups, including straight-chain alkyl groups, branched-chain alkyl, cycloalkyl (alicyclic), alkyl substituted cycloalkyl groups, and cycloalkyl substituted alkyl. In preferred forms, a straight chain or branched chain alkyl has 30 or fewer carbon atoms in its backbone (e.g., C$_1$-C$_{30}$ for straight chains, C$_3$-C$_{30}$ for branched chains), preferably 20 or fewer, more preferably 15 or fewer, most preferably 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred forms, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

The term "hydroxyalkyl" means an alkyl radical as defined herein, substituted with one or more, preferably one, two or three hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)2-hydroxyethyl.

The terms "alkoxyl" or "alkoxy," "aroxy" or "aryloxy," generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits. A "lower alkoxy" group is an alkoxy group containing from one to six carbon atoms.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkenyl" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl" as used herein is any $C_5$-$C_{26}$ carbon-based aromatic group, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

"Aralkyl" refers to an alkyl group which is substituted with an aryl group. Some non-limiting examples of aralkyl include benzyl and phenethyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Styryl" refers to a univalent radical $C_6H_5$—CH=CH— derived from styrene.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

"Carbonyl," as used herein, is art-recognized and includes such moieties as can be represented by the general formula:

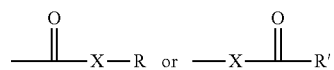

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R'', or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R''; R'' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

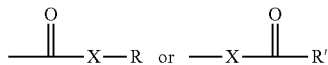

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

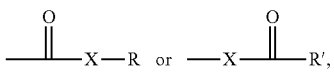

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred forms, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in R are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "amide" or "amido" are used interchangeably, refer to both "unsubstituted amido" and "substituted amido" and are represented by the general formula:

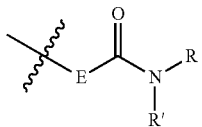

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide. In preferred forms, R and R' each independently represent a hydrogen atom, substituted or unsubstituted alkyl, a substituted or unsubstituted alkenyl, or $-(CH_2)_m-R'''$. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

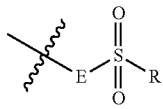

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

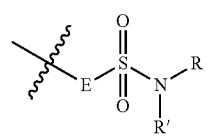

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide.

The term "phosphonyl" is represented by the formula

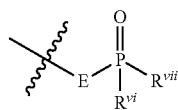

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R$^{vi}$ and R$^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, R$^{vi}$ and R$^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, R$^{vi}$ and R$^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, R$^{vi}$ and R$^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. When two or more heteroaryls are involved, the chemical moiety can be referred to as a "polyheteroaryl."

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a "substituted polyheteroaryl."

The term "polyaralkyl" refers to polyaryl that is attached to an alkyl group. The polyaralkyl can be substituted or unsubstituted.

The term "polyheteroaralkyl" refers to a polyheteroaryl that is attached to an alkyl group. The polyheteroaralkyl can be substituted or unsubstituted.

The term "C$_3$-C$_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The term "ether" as used herein is represented by the formula AOA$^1$, where A and A$^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —NO$_2$.

The term "phosphate" refers to —O—PO$_3$.

The term "azide" or "azido" are used interchangeably to refer to —N$_3$.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The compounds and substituents can be substituted with, independently, with the substituents described above in the definition of "Substituted."

The terms "effective amount" and "therapeutically effective amount," used interchangeably, as applied to the compounds, antibiotics, and pharmaceutical compositions described herein, mean the quantity necessary to render the desired therapeutic result. For example, an effective amount is a level effective to treat, cure, or alleviate the symptoms of a disease for which the composition and/or antineoplastic, or pharmaceutical composition, is/are being administered. Amounts effective for the particular therapeutic goal sought will depend upon a variety of factors including the disease being treated and its severity and/or stage of development/progression; the bioavailability and activity of the specific compound and/or antineoplastic, or pharmaceutical composition, used; the route or method of administration and introduction site on the subject; the rate of clearance of the specific composition and other pharmacokinetic properties; the duration of treatment; inoculation regimen; drugs used in combination or coincident with the specific composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for an individual patient.

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 15 82, 83, 84, 85, 86, 87, 88, 89, 90, 91, 92, 93, 94, 95, 96, 97, 98, 99, or 100%.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

As used herein, "treatment" or "treating" refers to arresting or inhibiting, or attempting to arrest or inhibit, the development or progression of a disease and/or causing, or attempting to cause, the reduction, suppression, regression, or remission of a disease and/or a symptom thereof. As would be understood by those skilled in the art, various clinical and scientific methodologies and assays may be used to assess the development or progression of an infection, and similarly, various clinical and scientific methodologies and assays may be used to assess the reduction, regression, or remission of an infection or its symptoms. "Treatment" refers to both therapeutic treatment and prophylactic or preventative measures. Those in need of treatment include those already with the infection as well as those prone to have the disease or those in whom the disease is to be prevented.

II. Compositions

A. Compounds

Daptomycin, approved by the FDA in 2003, stands as a good example of antibacterial cyclic lipopeptides. Daptomycin is a cyclic lipodepsipeptide containing 13 amino acids, 10 of which make up a 31-membered ring and three are anchored as an exocyclic tail with the N-terminal containing an n-decanoyl lipid. Within this structure are two unnatural amino acids, L-kynurenine (Kyn) and L-3-methylglutamic acid (3-mGlu).

Cyclic lipopeptides having one or more modifications relative to daptomycin are provided. The disclosed cyclic lipopeptides are also referred to as daptomycin analogues. The cyclic lipopeptides can possess antibiotic properties. The cyclic lipopeptides include those having alkylated or acylated kynurenine to replace Kyn13, N-methyl indol-3-ylmethyl, i.e., MeTrp, 1-naphthylmethyl, or 2-naphthylmethyl to replace Trp1, sarcosine to replace Gly5, dialkylated Orn to replace Orn6, and/or using 2,3-diaminobutyric acid or 2,3-diaminopropionic acid to replace Thr4. That is, at least one of the five general modifications described in the previous sentence is implemented to provide the cyclic lipopeptides. In specific embodiments, the modification involves methylation (or dimethylation with regard to Orn) at one or more of Gly (e.g., the Gly that is between Thr and Orn), Orn, Kyn, and/or Trp.

The cyclic lipopeptides have the general formula:

(I)

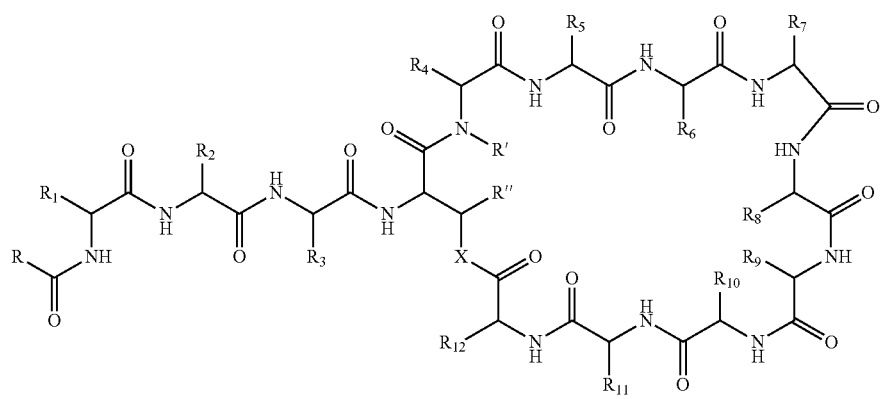

Formula I wherein, $R_1$-$R_{12}$ are independently substituted polyheteroaralkyl, unsubstituted polyheteroaralkyl, substituted polyaralkyl, unsubstituted polyaralkyl, substituted aralkyl, unsubstituted aralkyl, substituted alkyl, unsubstituted alkyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, unsubstituted $C_3$-$C_{20}$ cycloalkynyl, hydrogen, substituted alkenyl, unsubstituted alkenyl, substituted alkynyl, unsubstituted alkynyl, or a side chain of any natural or unnatural amino acid. Preferably, R1 is substituted polyheteroaralkyl, unsubstituted polyheteroaralkyl, substituted polyaralkyl, unsubstituted polyaralkyl, substituted aralkyl, unsubstituted aralkyl, substituted alkyl, unsubstituted alkyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, most preferably, R1 is the side chain of Trp (indol-3-ylmethyl), MeTrp (i.e. the nitrogen atom of the indole ring is methylated, N-methyl indol-3-ylmethyl), unsubstituted 1-naphthylmethyl, unsubstituted 2-naphthylmethyl, substituted 1-naphthylmethyl, or substituted 2-naphthylmethyl. Preferably $R_2$-$R_{12}$ are independently the side chain of any natural or unnatural amino acid;

R' and R" are independently hydrogen, unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl. Preferably, R' is hydrogen or unsubstituted alkyl, most preferably, R' is H or methyl; preferably, R" is hydrogen, unsubstituted alkyl, or substituted alkyl. Most preferably, R" is H, methyl or ethyl;

X is O or NRa, wherein Ra is hydrogen, unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl. Preferably, Ra is hydrogen;

R is substituted aryl, unsubstituted aryl, substituted alkenyl, unsubstituted alkenyl, substituted alkyl, substituted alkyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl. Preferably, R is a substituted aryl or substituted alkenyl.

In some forms of Formula I, at least one of R, $R_1$-$R_{12}$, R', and R" is substituted aryl, unsubstituted aryl, substituted alkenyl, unsubstituted alkenyl, —$(CH_2)_x$—$NR^*_2$, substituted polyheteroaralkyl, substituted polyaralkyl, unsubstituted polyaralkyl, substituted aralkyl, unsubstituted aralkyl, or substituted alkyl containing a substituted aniline, wherein x is an integer between one and ten, inclusive (e.g. 1, 2, 3, 4, 5, 6, 7, 8, 9, and 10), each R* is independently unsubstituted alkyl, substituted alkyl, substituted aryl, or unsubstituted aryl. Preferably, when present, R is substituted aryl or substituted alkenyl; x is three; each R* is independently unsubstituted alkyl, substituted alkyl, substituted aryl, or unsubstituted aryl, preferably are both unsubstituted alkyl (e.g. methyl); $R_1$ is substituted polyheteroaralkyl (e.g. N-alkylated indol-3-ylalkyl such as N-alkylated indol-3-ylmethyl), unsubstituted polyalkyl (e.g. 1-naphthylalkyl and 2-naphthylalkyl such as 1-naphthylmethyl and 2-naphthylmethyl, respectively); R' is hydrogen, unsubstituted alkyl (e.g. methyl), substituted alkyl, unsubstituted aryl, or unsubstituted aryl; R" is hydrogen, unsubstituted alkyl (e.g.

methyl and ethyl), substituted alkyl, unsubstituted aryl, or unsubstituted aryl; and R12 is a substituted alkyl containing a substituted aniline.

In some forms, R' is unsubstituted alkyl, substituted alkyl, unsubstituted aryl, or substituted aryl; $R_1$ is substituted polyheteroaralkyl or unsubstituted polyaralkyl; $R_2$-$R_{12}$ are independently the side chain of any natural or unnatural amino acid; and R is a substituted alkenyl or a substituted aryl.

In some forms, the cyclic lipopeptide has the formula:

(IV)

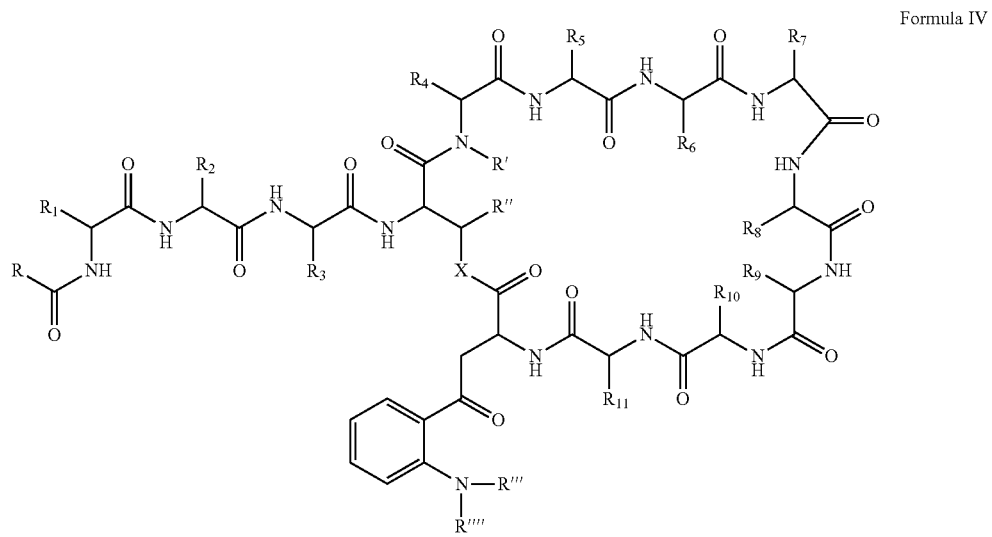

Formula IV wherein, $R_1$-$R_{11}$ are independently unsubstituted polyheteroaralkyl, substituted polyheteroaralkyl, unsubstituted polyaralkyl, polyaralkyl, or the side chain of any natural or unnatural amino acid; and R''' and R'''' are independently hydrogen, unsubstituted alkyl, unsubstituted alkyl, unsubstituted alkyl, unsubstituted aryl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, or unsubstituted phosphonyl. In some forms, at least one of R''' and R''' is not hydrogen. Preferably R''' is hydrogen, R'''' is unsubstituted alkyl (e.g. methyl, such that $R_{12}$ is N-methylkynurenine), or substituted carbonyl (e.g. acyl).

Preferably, R', R'', and R''' are independently H, unsubstituted alkyl (e.g. methyl, ethyl) or substituted alkyl, R'''' is substituted carbonyl (e.g. acyl) or unsubstituted alkyl (e.g. methyl), or substituted alkyl, X is O or NH; and R is unsubstituted $C_5$-$C_{14}$ alkyl, substituted C5-C14 alkyl, unsubstituted C5-C14 alkenyl, substituted C5-C14 alkenyl, unsubstituted C5-C14 alkynyl, substituted C5-C14 alkynyl, unsubstituted C5-C14 aryl, substituted C5-C14 aryl, unsubstituted C5-C14 polyaryl, substituted C5-C14 polyaryl, unsubstituted C5-C14 polyheteroaryl, or substituted C5-C14 polyheteroaryl. An example of a substituted C5-C14 alkenyl can be (E)-2-(4-pentylphenyl) propenyl, while an example of a substituted C5-C14 aryl can be 4-(phenylethynyl) phenyl.

In some forms of Formula IV, R''' is hydrogen, unsubstituted alkyl, or substituted alkyl, and R''' is unsubstituted alkyl, substituted alkyl, unsubstituted aryl, or substituted aryl.

In some forms, the cyclic lipopeptide is as described above for Formula IV, wherein, $R_1$ is unsubstituted polyheteroaralkyl (e.g. the side chain of Trp, i.e., indol-3-ylmethyl), substituted polyheteroaralkyl (e.g. MeTrp, i.e., the nitrogen atom of the indole ring is methylated, such as N-methyl indol-3-ylmethyl), unsubstituted polyaralkyl (e.g. 1-naphthylmethyl or 2-naphthylmethyl), or substituted polyaralkyl; and R2-R11 are independently the side chain of any natural or unnatural amino acid.

In some forms, the cyclic lipopeptide has the formula:

(V)

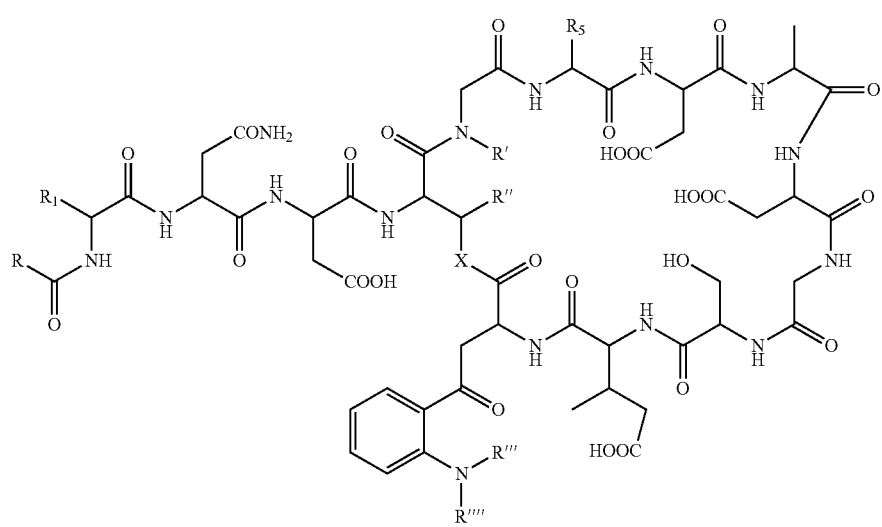

Formula V wherein, $R_1$ is unsubstituted polyheteroaralkyl (e.g. the side chain of Trp, i.e., indol-3-ylmethyl), substituted polyheteroaralkyl (e.g. MeTrp, i.e., the nitrogen atom of the indole ring is methylated, i.e., N-methyl indol-3-yl), unsubstituted polyaralkyl (e.g. 1-naphthylmethyl or 2-naphthylmethyl), or substituted polyaralkyl, and $R_5$ is the side chain of amino acid, natural or unnatural. Preferably, R' is H or unsubstituted alkyl (e.g. methyl); R" is H, unsubstituted alkyl (e.g. methyl or ethyl), R''' is H or unsubstituted alkyl (e.g. methyl); R'''' is substituted carbonyl (e.g. acyl) or unsubstituted alkyl (e.g. methyl); X is O or NH; and R is a unsubstituted C5-C14 alkyl, substituted C5-C14 alkyl, unsubstituted C5-C14 alkenyl, substituted C5-C14 alkenyl, unsubstituted C5-C14 alkynyl, substituted C5-C14 alkynyl, unsubstituted C5-C14 aryl, substituted C5-C14 aryl, unsubstituted C5-C14 polyaryl, substituted C5-C14 polyaryl, unsubstituted C5-C14 polyheteroaryl, or substituted C5-C14 polyheteroaryl. An example of a substituted C5-C14 alkenyl can be (E)-2-(4-pentylphenyl) propenyl, while an example of a substituted C5-C14 aryl can be 4-(phenylethynyl)phenyl.

In some forms of Formula I, R has the formula:

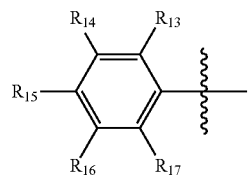

Formula IX wherein $R_{13}$, $R_{14}$, $R_{15}$, $R_{16}$, and $R_{17}$ are independently hydrogen, unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, unsubstituted phosphonyl, hydroxyl, halogen, cyano, or nitro. Preferably, at least one of $R_{13}$-$R_{17}$ is not hydrogen.

In some forms of Formula IX, at least one of $R_{13}$-$R_{17}$ is a substituted alkynyl.

In some forms of the cyclic lipopeptide, R has the formula:

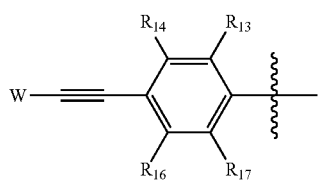

Formula X wherein $R_{13}$, $R_{14}$, $R_{16}$, and $R_{17}$ are as described above for Formula IX, wherein W is substituted aryl, unsubstituted aryl, substituted heteroaryl, unsubstituted heteroaryl, substituted polyheteroaryl, unsubstituted polyheteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, unsubstituted $C_3$-$C_{20}$ cycloalkynyl, hydrogen, substituted alkyl, unsubstituted alkyl, substituted alkenyl, unsubstituted alkenyl, substituted alkynyl, or unsubstituted alkynyl.

In some forms, R is a substituted aryl, having the formula:

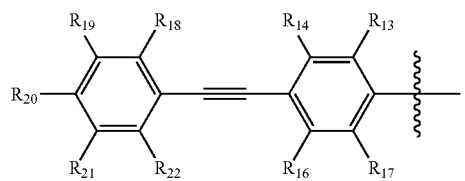

Formula XI wherein R13, R14, R16, and R17 are as described above for Formula IX, and wherein R18, R19, R20, R21, and R22 are independently hydrogen, unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, unsubstituted phosphonyl, hydroxyl, halogen, cyano, or nitro.

In some forms of Formula XI, R13, R14, R16, and R17 are hydrogen, four of R18, R19, R20, R21, and R22 are hydrogen, and one is unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, unsubstituted phosphonyl, hydroxyl, halogen, cyano, or nitro.

In some forms of Formula XI, R13, R14, R16, and R17 are hydrogen, four of R18, R19, R20, R21, and R22 are hydrogen, and one is unsubstituted alkyl, substituted alkyl, unsubstituted alkenyl, unsubstituted alkynyl, unsubstituted heteroaryl, unsubstituted $C_3$-$C_{20}$ heterocyclyl, hydroxyl, or nitro.

In some forms of Formula XI, R13, R14, R16, R17, and R18-R22 are hydrogen, i.e., R1 is 4-(phenylethynyl)phenyl,

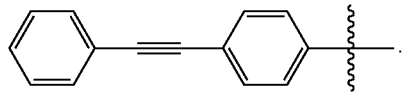

In some forms, R is a substituted alkenyl having the formula:

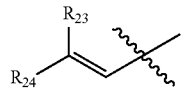

Formula XII wherein R23 and R24 are independently hydrogen, unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, unsubstituted phosphonyl, hydroxyl, halogen, cyano, or nitro. Preferably, at least one of R23 and R24 is not hydrogen.

In some forms of Formula XII, R23 and R24 are independently unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl.

In some forms of Formula XII, R23 is an unsubstituted alkyl.

In some forms of Formula XII, R24 is a substituted aryl or unsubstituted aryl.

In some forms of Formula XII, R23 is an unsubstituted alkyl, and R24 is a substituted aryl or unsubstituted aryl having the formula:

Formula XIII

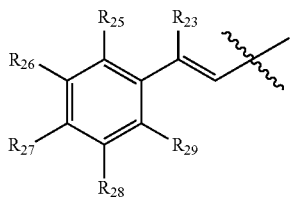

wherein R25, R26, R27, R28, and R29 are independently hydrogen, unsubstituted alkyl, substituted alkyl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, unsubstituted phosphonyl, hydroxyl, halogen, cyano, or nitro.

In some forms of Formula XIII, R27 is a substituted alkyl or unsubstituted alkyl group.

In some forms of Formula XIII, R27 is an unsubstituted alkyl group, and R25, R26, R28, R29 are each hydrogen.

In some forms of Formula XIII, R23 and R27 are unsubstituted alkyl groups, and R25, R26, R28, and R29 are each hydrogen.

In some forms of Formula XIII, R23 and R27 are independently unsubstituted C1-C10 alkyl groups, and R25, R26, R28, and R29 are each hydrogen.

In some forms of Formula XIII, R23 is an unsubstituted C1 alkyl group, R27 is an unsubstituted C5 alkyl group, and R25, R26, R28, and R29 are each hydrogen, i.e., R is

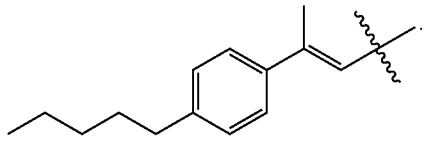 [SMILES: */C=C(\C)c1ccc(CCCCC)cc1]

Specific examples include when R5 is —(CH$_2$)$_3$—NR*$_2$, each R* is an alkyl group; each R* is methyl; R1 is MeTrp; R1 is methyl; R12 is MeKyn; R1 is 1-naphthylalanine; R1 is 2-naphthylalanine; and R is

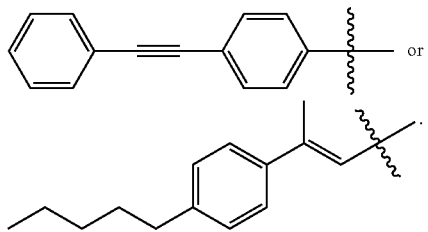

In some forms, the cyclic lipopeptide contains a methylated Kyn having the formula:

(Va)

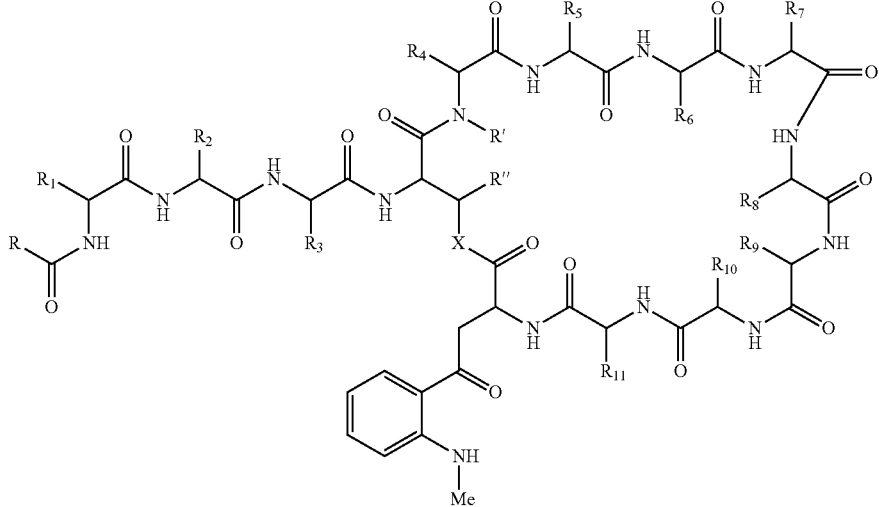

Formula Va wherein,

R1-R11 are independently unsubstituted polyheteroaralkyl, substituted polyheteroaralkyl, unsubstituted polyaralkyl, polyaralkyl, or the side chain of any natural or unnatural amino acid.

Preferably, R' is H or unsubstituted alkyl (e.g. methyl); R'' is H, unsubstituted alkyl (e.g. methyl or ethyl); and R is a unsubstituted C5-C14 alkyl, substituted C5-C14 alkyl, unsubstituted C5-C14 alkenyl, substituted C5-C14 alkenyl, unsubstituted C5-C14 alkynyl, substituted C5-C14 alkynyl, unsubstituted C5-C14 aryl, substituted C5-C14 aryl, unsubstituted C5-C14 polyaryl, substituted C5-C14 polyaryl, unsubstituted C5-C14 polyheteroaryl, or substituted C5-C14 polyheteroaryl. An example of a substituted C5-C14 alkenyl can be (E)-2-(4-pentylphenyl) propenyl, while an example of a substituted C5-C14 aryl can be 4-(phenylethynyl) phenyl.

In some forms, the cyclic lipopeptide has the formula:

stituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl.

In some forms of Formula VII, R', Rb, Rc, and Rd are independently hydrogen, substituted alkyl, or unsubstituted alkyl (such as methyl, ethyl, etc.).

In some forms of Formula VII, Rb is H, or methyl; R' is H or methyl or ethyl; Rc and Rd are independently H, or methyl; X is O or NH; and R is unsubstituted C5-C14 alkyl, substituted C5-C14 alkyl, unsubstituted C5-C14 alkenyl, substituted C5-C14 alkenyl, unsubstituted C5-C14 alkynyl, substituted C5-C14 alkynyl, unsubstituted C5-C14 aryl, (VII)

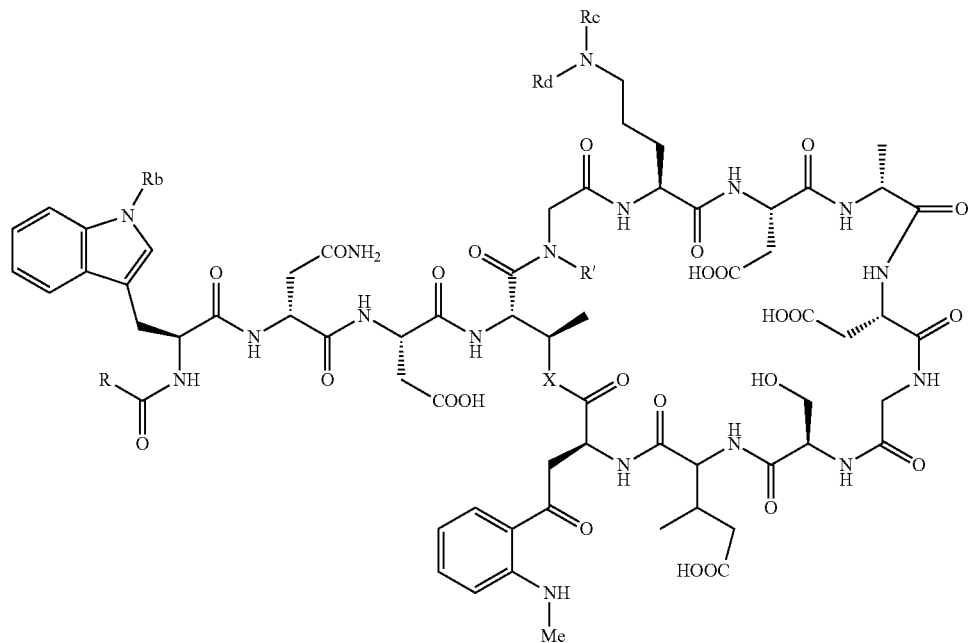

Formula VII wherein,

R', Rb, Rc, and Rd are independently hydrogen, unsubstituted alkyl, substituted alkyl, substituted alkenyl, unsubsubstituted C5-C14 aryl, unsubstituted C5-C14 polyaryl, substituted C5-C14 polyaryl, unsubstituted C5-C14 polyheteroaryl, or substituted C5-C14 polyheteroaryl.

In some forms, the cyclic lipopeptide has the formula:

(VIII)

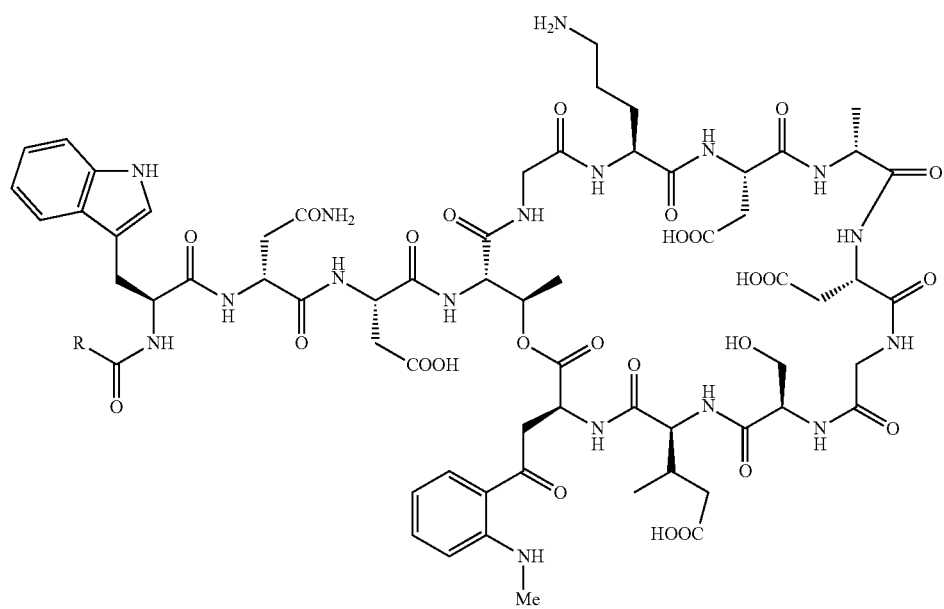

Formula VIII

In some forms of Formula VIII, R is R is unsubstituted C5-C14 alkyl, substituted C5-C14 alkyl, unsubstituted C5-C14 alkenyl, substituted C5-C14 alkenyl, unsubstituted C5-C14 alkynyl, substituted C5-C14 alkynyl, unsubstituted C5-C14 aryl, substituted C5-C14 aryl, unsubstituted C5-C14 polyaryl, substituted C5-C14 polyaryl, unsubstituted C5-C14 polyheteroaryl, or substituted C5-C14 polyheteroaryl, preferably R is C9H19 or (E)-2-(4-pentylphenyl)propenyl.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound or subgroup of compounds can be either specifically included for or excluded from use or included in or excluded from a list of compounds. For example, any one or more of the compounds described herein, with a structure depicted herein, or referred to in the Tables or the Examples herein can be specifically included, excluded, or combined in any combination, in a set or subgroup of such compounds. Such specific sets, subgroups, inclusions, and exclusions can be applied to any aspect of the compositions and methods described here. For example, a set of compounds that specifically excludes one or more particular compounds can be used or applied in the context of compounds per se (for example, a list or set of compounds), compositions including the compound (including, for example, pharmaceutical compositions), any one or more of the disclosed methods, or combinations of these. Different sets and subgroups of compounds with such specific inclusions and exclusions can be used or applied in the context of compounds per se, compositions including one or more of the compounds, or any of the disclosed methods. All of these different sets and subgroups of compounds—and the different sets of compounds, compositions, and methods using or applying the compounds—are specifically and individual contemplated and should be considered as specifically and individually described. As an example, any of the natural amino acids or unnatural amino acids, as defined above, can be specifically included or excluded, as a group or individually, from any position in the compounds per se (for example, a list or set of compounds), from compounds in compositions (including, for example, pharmaceutical compositions), or any one or more of the disclosed methods, or combinations of these. Further, specific cyclic compounds can excluded from the list of compounds. As an example, daptomycin can be excluded.

B. Pharmaceutical Compositions and Routes of Administration

Pharmaceutical compositions including one or more of the disclosed compounds are also provided. The compositions can be formulated in dosage forms appropriate for each route of administration. Daptomycin is most typically administered by infusion (e.g., 30 min) or injection (e.g., 2 min). Studies also show efficacy with topical delivery, which can be enhanced when the formulation includes a delivery vehicle such liposomes (see, e.g., Mengeloglu, et al., *J Ocul Pharmacol Ther.* 2013 December; 29(10):893-9. doi: 10.1089/jop.2013.0120. Epub 2013 Sep. 26, and Li, et al., *Int J Nanomedicine.* 2013; 8:1285-92. doi: 10.2147/IJN.S41695. Epub 2013 Mar. 24).

Preferred routes of administration for the disclosed lipopeptides therefore include parenteral, particularly intravenous injection or infusion, and topical, though alternations in the composition of the disclosed compounds may improve its delivery by other routes, for example oral, relative to daptomycin. Thus in some embodiments, a cyclic lipopeptide described herein or pharmaceutical compositions including one or more lipopeptides is administered orally, parenterally, by inhalation, topically, transdermal (either passively or using iontophoresis or electroporation), or transmucosal (nasal, vaginal, rectal, buccally, or sublingual), or by an implanted reservoir, external pump, or catheter. The cyclic lipopeptides described herein can be directly injected or administered into an abscess, ventricle, or joint. Parenteral administration includes intraperitoneal, subcutaneous, intravenous (IV), intramuscular, intra-articular, intra-synovial, cisternal, intrathecal, intrahepatic, intralesional, and intracranial injection or infusion. The compositions may also be administered using bioerodible inserts and may be delivered directly to an appropriate target tissue or organ.

The pharmaceutical compositions typically include an effective amount of a disclosed compound. The precise dosage will vary according to a variety of factors such as subject-dependent variables (e.g., age, immune system health, etc.), the disease, and the treatment being effected. Dosages are discussed in more detail below.

1. Formulations for Parenteral Administration

In a preferred embodiment, the disclosed compounds are administered in an aqueous solution, by parenteral injection or infusion. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

Compositions containing one or more of the disclosed compounds can be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. The matrix can also be incorporated into or onto a medical device to, for example, prevent infection or to aid in healing. In some embodiments, a matrix is used to facilitate healing of pressure sores, decubitis ulcers, etc.

Either non-biodegradable or biodegradable matrices can be used for delivery of compounds, although biodegradable matrices are preferred. For example, liposomal or polymeric encapsulation may be used to formulate the compositions. The polymers can be natural or synthetic, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection and typically deliver a dosage that is much less than the dosage for treatment of an entire body. The devices can also be formulated for systemic delivery. These can be implanted or injected subcutaneously.

3. Topical

These will typically be ointments, creams, gels, oils, foams, lotions, sprays, or patches, all of which can be prepared using standard technology. Such formulations can be used for local delivery, for example on/to the skin, as well as regional and even systemic delivery. Buffers can be used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof, preferably without reducing the active of the lipopeptide. Chemical penetrations and methods of increasing transdermal drug delivery are known in the art, see, for example, Inayat, et al., *Tropical Journal of Pharmaceutical Research*, 8(2):173-179 (2009) and Fox, et al., *Molecules*, 16:10507-10540 (2011).

III. Methods of Use

The administration methods can be used for human patients in clinical applications and in veterinary applications. The methods typically include administering a subject in need thereof an effective amount of one or more the disclosed peptides, or a pharmaceutical composition thereof. Exemplary subjects in need thereof have an infection or in danger of contracting an infection, particularly a bacterial infection. In the most preferred embodiments the subject has or is at risk of having a gram-positive bacterial infection.

A. Exemplary Dosages and Treatment Regimens

The dose and dosage interval for the methods are those that are safe and efficacious in clinical or veterinary applications. In some embodiments, the administration methods involve longer dosing intervals (such as once-daily or longer) with higher doses (such as 15 mg/kg or more) of the cyclic lipopeptides described herein. In other embodiments, the administration methods involve relatively shorter dosing intervals (such as twice-daily or shorter) with lower doses (such as 15 mg/kg or less) of the cyclic lipopeptides described herein.

The cyclic lipopeptides described herein can be administered once-daily, twice-daily, or thrice-daily. Daptomycin is known to have skeletal muscle toxicity, especially when the time between doses is relatively short. Once-daily administration of the cyclic lipopeptides described herein can provide greater time between doses compared to multiple daily doses. In some instances, once-daily administration of the cyclic lipopeptides described herein permits repair of subclinical muscle damage that may be associated with using the cyclic lipopeptides described herein and thereby avoid long term and/or permanent physical damage. In other words, in some embodiments, once-daily dosing of the cyclic lipopeptides described herein results in less toxicity.

For example, the dose can be 1 to 100 mg/kg of the cyclic lipopeptides described herein. In another embodiment, the dose is 5 to 50 mg/kg of the cyclic lipopeptides described herein. In yet another embodiment, the dose for humans patients is 2 to 15 mg/kg. In still yet another embodiment, the dose for humans patients is 3 to 12 mg/kg of the cyclic lipopeptides described herein. Examples of specific doses that may be used include 7, 8, 9, 10, 11, 12, 13, 14, 16, 18, 20, 22 or 25 mg/kg of the cyclic lipopeptides described herein. In some embodiments for veterinary applications, the dose is 2 to 40 mg/kg of the cyclic lipopeptides described herein.

In some embodiments, the cyclic lipopeptides described herein can be administered in a smaller dose compared to the administration of daptomycin. In one embodiment, the cyclic lipopeptides described herein can be administered in a 10% smaller dose compared to the administration of daptomycin to the same patient for the same ailment. In another embodiment, the cyclic lipopeptides described herein can be administered in a 25% smaller dose compared to the administration of daptomycin to the same patient for the same ailment. In yet another embodiment, the cyclic lipopeptides described herein can be administered in a 40% smaller dose compared to the administration of daptomycin to the same patient for the same ailment.

In some embodiments, the dosage interval of the cyclic lipopeptides described herein is from 6 hours to weekly. In specific embodiments, the cyclic lipopeptides described herein is administered at a dosage interval of once every 12 hours, once every 24 hours, once every 48 hours, once every 72 hours, once every 96 hours, or once weekly. Administration at less frequent dosage intervals, such as once every 96 hours or once weekly, may be desirable for patients who have impaired renal function or who require hemodialysis. The dosage interval for veterinary applications may be somewhat shorter or longer than the dosage intervals for human patients, depending upon whether the cyclic lipopeptides described herein has a shorter or longer half-life, respectively, in a particular animal species compared to in humans. Specific dosage intervals for both clinical and veterinary applications can be determined by one skilled in the art following the methods described herein.

In some embodiments, the administration method includes administering a dose of 1 to 100 mg/kg of a cyclic lipopeptide described herein once every 6 hours to once weekly. In some embodiments, a cyclic lipopeptide described herein is administered in a dose of 5 to 50 mg/kg once every 24, 48, 72, or 96 hours.

The cyclic lipopeptides described herein can be administered until the bacterial infection is eradicated or reduced. In one embodiment, the cyclic lipopeptides described herein are administered for a period of time from 3 days to 6 months. In another embodiment, the cyclic lipopeptides described herein are administered for 7 to 50 days. In yet another embodiment, the cyclic lipopeptides described herein are administered for 10 to 20 days.

The methods of using the cyclic lipopeptides described herein include administering the cyclic lipopeptide to a patient in need thereof in an amount that is efficacious in reducing or eliminating a gram-positive bacterial infection. The methods also include administering the cyclic lipopeptide to a patient in need thereof in an amount that is efficacious in reducing or eliminating a gram-positive bacterial infection and that results in reduced skeletal muscle toxicity compared to other methods, for example those that include administering daptomycin, other lipopeptide antibiotics, or quinupristin/dalfopristin.

B. Subjects to be Treated

The methods can be used to treat a patient having a bacterial infection in which the infection is caused or exacerbated by any type of gram-positive bacteria. In an embodiment, the cyclic lipopeptides described herein is administered to a patient according to the methods described herein. In one embodiment, the bacterial infection can be caused or exacerbated by bacteria including one or more of, but not limited to, methicillin-susceptible and methicillin-resistant *staphylococci* (including *Staphylococcus aureus, Staphylococcus epidermidis, Staphylococcus haemolyticus, Staphylococcus hominis, Staphylococcus saprophyticus*, and coagulase-negative *staphylococci*), glycopeptide intermediary-susceptible *Staphylococcus aureus* (GISA), penicillin-susceptible and penicillin-resistant *streptococci* (including *Streptococcus pneumoniae, Streptococcus pyogenes, Streptococcus agalactiae, Streptococcus avium, Streptococcus bovis, Streptococcus lactis, Streptococcus sangius* and *Streptococci* Group C, *Streptococci* Group G and *viridans streptococci*), enterococci (including vancomycin-susceptible and vancomycin-resistant strains such as *Enterococcus faecalis* and *Enterococcus faecium*), *Clostridium difficile, Clostridium clostridiiforme, Clostridium innocuum, Clostridium perfringens, Clostridium ramosum, Haemophilus influenzae, Listeria monocytogenes, Corynebacterium jeikeium, Bifidobacterium* spp., *Eubacterium aerofaciens, Eubacterium lentum, Lactobacillus acidophilus, Lactobacillus casei, Lactobacillus plantarum, Lactococcus* spp., *Leuconostoc* spp., *Pediococcus, Peptostreptococcus anaerobius, Peptostreptococcus asaccarolyticus, Peptostreptococcus magnus, Peptostreptococcus micros, Peptostreptococcus prevotii, Peptostreptococcus productus, Propionibacterium acnes*, and *Actinomyces* spp.

The antibacterial activity of the cyclic lipopeptides described herein against classically "resistant" strains can be comparable to that against classically "susceptible" strains. In some embodiments, the cyclic lipopeptide described herein is administered according to a patient who exhibits a bacterial infection that is resistant to other antibiotics. In addition, unlike glycopeptide antibiotics, the cyclic lipopeptides described herein can exhibit rapid, concentration-dependent bactericidal activity against gram-positive organisms. In another embodiment, the cyclic lipopeptide described herein is administered to a patient in need of rapidly acting antibiotic therapy.

The cyclic lipopeptides described herein can be used for a gram-positive bacterial infection of any organ or tissue in the body. Examples of organs or tissue include one or more of, without limitation, skeletal muscle, skin, bloodstream, kidneys, heart, lung, and bone. The cyclic lipopeptides described herein can be used to treat one or more of, without limitation, skin and soft tissue infections, bacteremia, and urinary tract infections. The cyclic lipopeptides described herein can be used to treat community acquired respiratory infections, including one or more of, without limitation, otitis media, sinusitis, chronic bronchitis and pneumonia, including pneumonia caused by drug-resistant *Streptococcus pneumoniae* or *Haemophilus influenzae*. The cyclic lipopeptides described herein can be used to treat mixed infections that comprise different types of gram-positive bacteria, or which comprise both gram-positive and gram-negative bacteria. Examples of such infections include intra-abdominal infections and obstetrical/gynecological infections. The cyclic lipopeptides described herein can be used in step down therapy for hospital infections, including one or more of, without limitation, pneumonia, intra-abdominal sepsis, skin and soft tissue infections, and bone and joint infections. The cyclic lipopeptides described herein can be used to treat an infection including one or more of, without limitation, endocarditis, septic arthritis, and osteomyelitis.

C. Combination Therapies

The methods of using the cyclic lipopeptide described herein can include concurrently administering with one or more additional therapeutic, diagnostic, or prophylactic agents, for example an antibiotic other than a lipopeptide antibiotic. The lipopeptide and the additional therapeutic, diagnostic, or prophylactic agent can be in the same or different admixtures or pharmaceutical compositions. The cyclic lipopeptide described herein can exhibit high plasma protein binding and may be unable to cross cell membranes. In this context, the cyclic lipopeptide described herein is unlikely to cause interactions with other antibiotics. Consequently, the cyclic lipopeptides described herein can in some embodiments work in a complimentary fashion or even more than additively with one or more co-administered non-lipopeptide antibiotic. Moreover, the cyclic lipopeptides described herein can improve the toxicity profile of one or more co-administered non-lipopeptide antibiotics.

Examples of antibiotics and classes thereof that may be co-administered with the cyclic lipopeptides described herein (non-lipopeptide antibiotics) include one or more of, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, and viomycin. In specific embodiments, non-lipopeptide antibiotics that can be co-administered with the cyclic lipopeptides described herein include one or more of, without limitation, imipenen, amikacin, netilmicin, fosfomycin, gentamicin, ceftriaxone, and teicoplanin.

IV. Methods of Making

The cyclic lipopeptides described herein, can be synthesized using a variety of methods known to those of skill art including, but not limited to, chemical synthesis, biochemical synthesis, chemoenzymatic synthesis, semisynthesis, or a combination thereof. Preferably, the cyclic lipopeptides can be produced via chemical synthesis. The chemical synthetic approaches can be via solid phase synthesis, solution phase synthesis, or a combination thereof. Preferably, the cyclic lipopeptides can be synthesized using a hybrid approach that involves both solid phase and solution phase synthetic approaches. The synthesis can be performed on a resin, such as 2-chlorotrityl chloride resin (with a resin loading of 0.4 mmol/g), under standard Fmoc/tBu protocols of solid phase peptide synthesis. The deblock mixture can be a mixture of 20/80 (v/v) of piperidine/DMF. Fmoc protected amino acids that can be used include, but are not limited to, Fmoc-Ala-OH, Fmoc-DAla-OH, Fmoc-Arg(Pbf)-OH, Fmoc-Asn(Trt)-OH, Fmoc-DAsn(Trt)-OH Fmoc-Asp(tBu)-OH, Fmoc-Glu(tBu)-OH, Fmoc-Gln(Trt)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Boc-DSer(tBu)-OH, Fmoc-meTrp-OH, Fmoc-meKyn-OH, Fmoc-acKyn-OH, Fmoc-1Nal-OH and Fmoc-2Nal-OH. Upon completion of the synthesis, the peptide resin can be subjected to a cleavage cocktail, followed by filtering of the resin, and the filtrates are blown off under a stream of condensed air. The crude product can be triturated with cold diethyl ether to give a white suspension, which is centrifuged and the ether subsequently decanted. The remaining solid can be purified via HPLC purification.

EXAMPLES

Following are examples that illustrate embodiments for practicing the invention. These examples should not be construed as limiting. All percentages are by weight and all solvent mixture proportions are by volume unless otherwise noted. Some of the examples described below, are also described in U.S. application Ser. No. 15/093,950, the entire contents of which are specifically incorporated herein, by reference.

The synthesis of these cyclic lipopeptides was demonstrated using a hybrid strategy using both solid phase and solution phase synthesis. Synthesis was performed manually on 2-chlorotrityl chloride Resin (resin loading: 0.4 mmol/g). Peptides were synthesized under standard Fmoc/tBu protocols. The deblock mixture was a mixture of 20/80 (v/v) of piperidine/DMF. The following Fmoc amino acids were employed: Fmoc-Ala-OH, Fmoc-DAla-OH, Fmoc-Arg(Pbf)-OH, Fmoc-Asn(Trt)-OH, Fmoc-DAsn(Trt)-OH Fmoc-Asp(tBu)-OH, Fmoc-Glu(tBu)-OH, Fmoc-Gln(Trt)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Boc-DSer(tBu)-OH, Fmoc-meTrp-OH, Fmoc-meKyn-OH, Fmoc-acKyn-OH, Fmoc-1Nal-OH and Fmoc-2Nal-OH. All natural amino acids and coupling reagents (Aldrich and GL Biochem) were commercially available and used without further purification. Upon completion of the synthesis, the peptide resin was subjected to a cleavage cocktail. The resin was filtered and the combined filtrates were blown off under a stream of condensed air. The crude product was triturated with cold diethyl ether to give a white suspension, which was centrifuged and the ether subsequently decanted. The remaining solid was ready for HPLC purification. Preparative HPLC was performed on a Waters system, using a Vydac 218TP™ C18 column (10 µm, 10×250 mm) or a Vydac 218TP™ C18 column (10 µm, 22×250 mm). Buffer A: 0.1% TFA in acetonitrile; buffer B: 0.1% TFA in $H_2O$.

Example 1. Synthesis of Compound 1

Linear peptide resin-Gly-Asp(tBu)-DAla-Asp(tBu)-Orn(Boc)-Gly-Thr[O-meKyn-mGlu(tBu)-DSer(tBu)]-Asp(tBu)-DAsn(Trt)-Trp(Boc)-$C_9H_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the methylated Kyn-containing daptomycin analogues Compound 1. Cald. $[M+H]^+$ 1635.7, found $[M+H]^+$ 1635.7, $[M+2H]^{2+}$ 818.1.

Compound 1

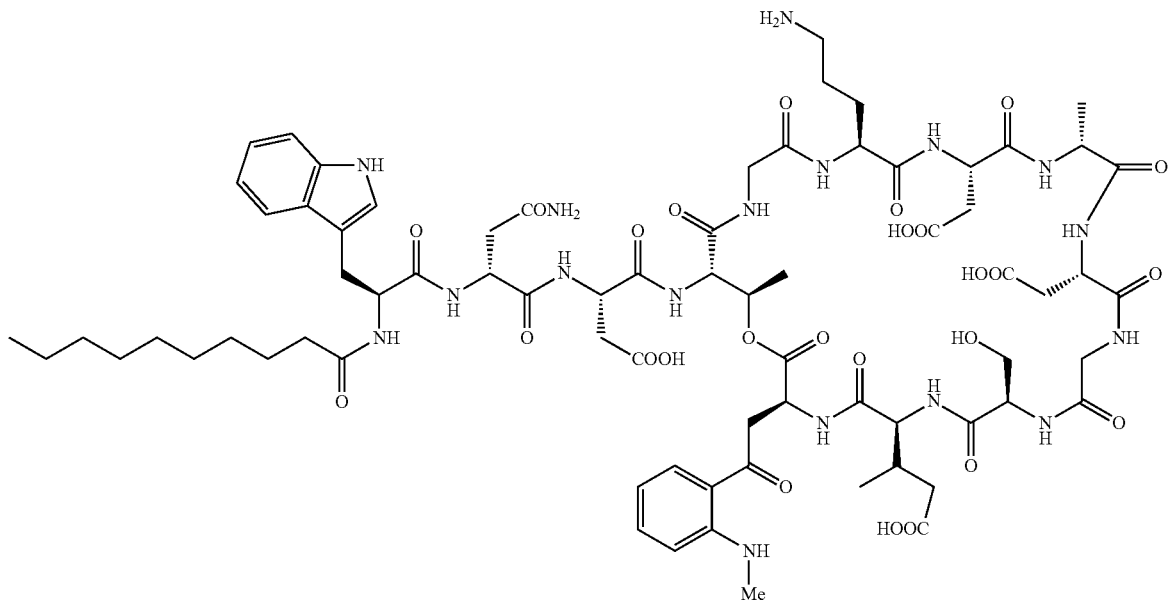

Example 2. Synthesis of Compound 2

Linear peptide resin-Gly-Asp(tBu)-DAla-Asp(tBu)-Orn(Boc)-Gly-Thr[O-Kyn-mGlu(tBu)-DSer(tBu)]-Asp(tBu)-DAsn(Trt)-meTrp-C$_9$H$_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the methylated Trp-containing daptomycin analogues Compound 2. Cald. [M+H]$^+$ 1635.7, found [M+H]$^+$ 1635.6, [M+2H]$^{2+}$ 818.0.

Compound 2

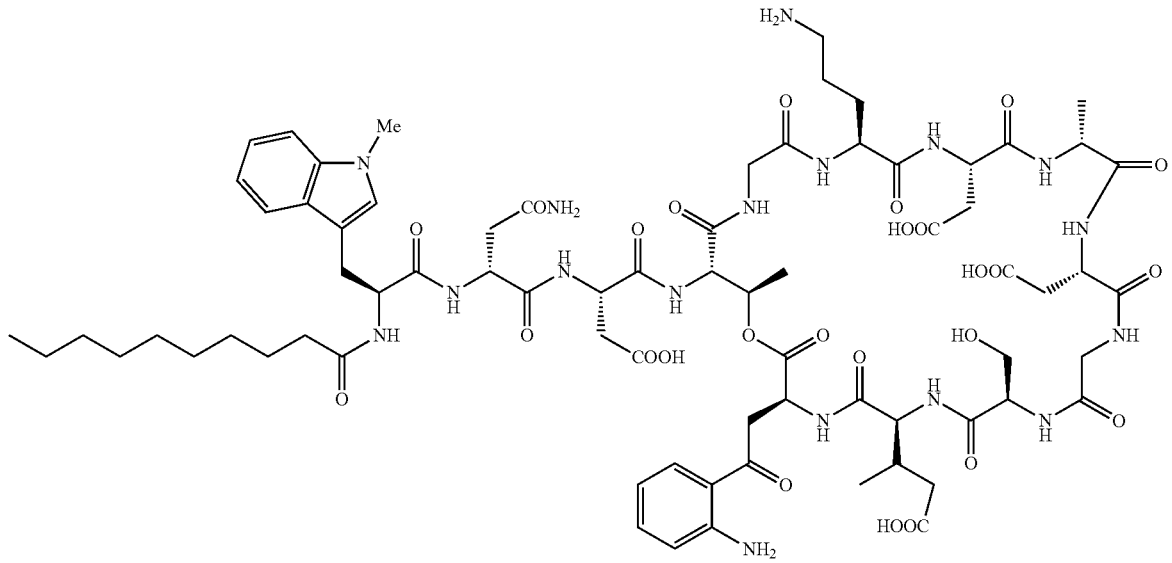

Example 3. Synthesis of Compound 3

Linear peptide resin-Gly-Asp(tBu)-DAla-Asp(tBu)-Orn(Boc)-Gly-Thr[O-Kyn-mGlu(tBu)-DSer(tBu)]-Asp(tBu)-DAsn(Trt)-1Nal-C$_9$H$_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the 1-naphthyl Ala-containing daptomycin analogues Compound 3. Cald. [M+H]$^+$ 1630.8, found [M+H]$^+$ 1630.8, [M+2H]$^{2+}$ 815.4.

Example 4. Synthesis of Compound 4

Linear peptide resin-Gly-Asp(tBu)-DAla-Asp(tBu)-Orn(Boc)-Sar-Thr[O-meKyn-mGlu(tBu)-DSer(tBu)]-Asp(tBu)-DAsn(Trt)-Trp(Boc)-C$_9$H$_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the Sar-containing daptomycin analogues Compound 4. Cald. [M+H]$^+$ 1648.7, found [M+H]$^+$ 1648.5, [M+2H]$^{2+}$ 823.9.

3

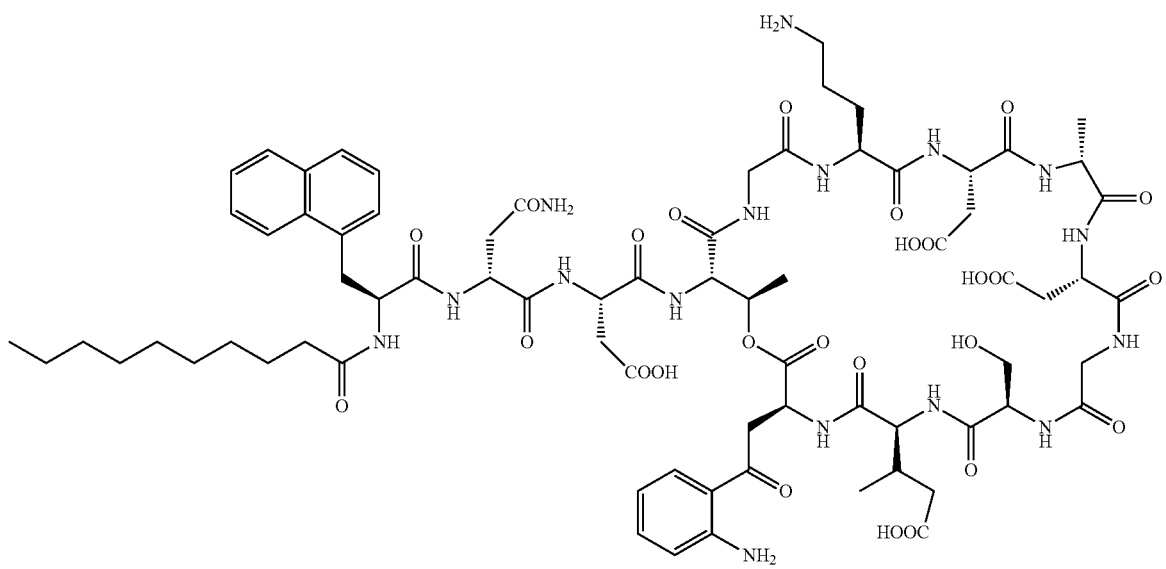

Compound 3

4

Compound 4

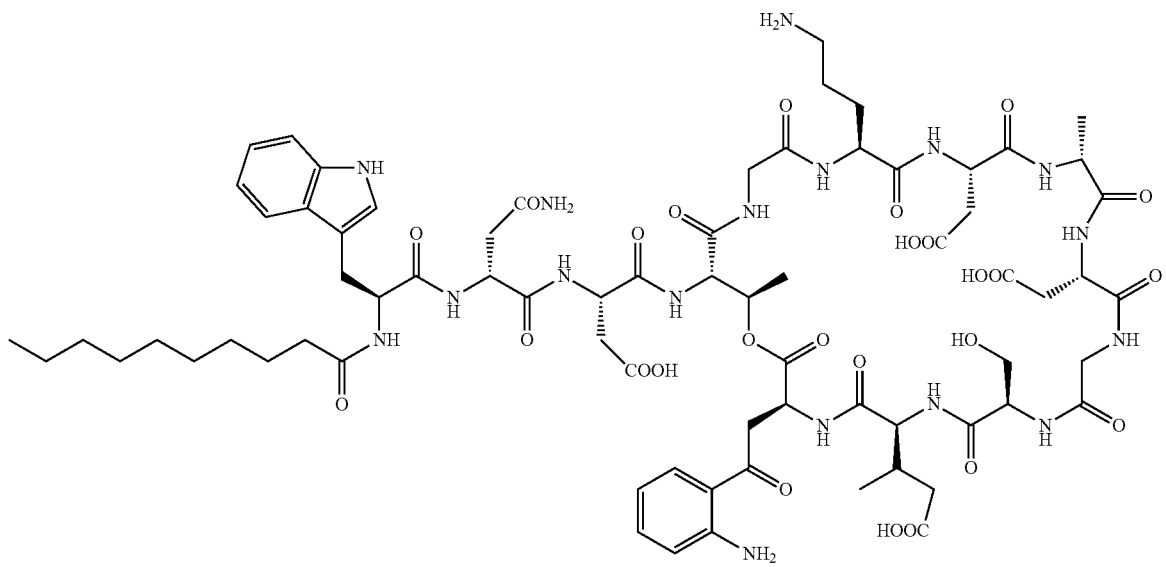

Example 5. Synthesis of Compound 5

Linear peptide resin-Gly-Asp(tBu)-DAla-Asp(tBu)-Orn(Boc)-Gly-Thr[O-Kyn-mGlu(tBu)-DSer(tBu)]-Asp(tBu)-DAsn(Trt)-Trp(Boc)-4-phenylethynyl-benzoyl was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the 4-phenylethynyl-benzoyl-containing daptomycin analogues Compound 5. Cald. [M+H]$^+$ 1671.6, found [M+H]$^+$ 1671.9, [M+2H]$^{2+}$ 836.1.

5

Compound 5

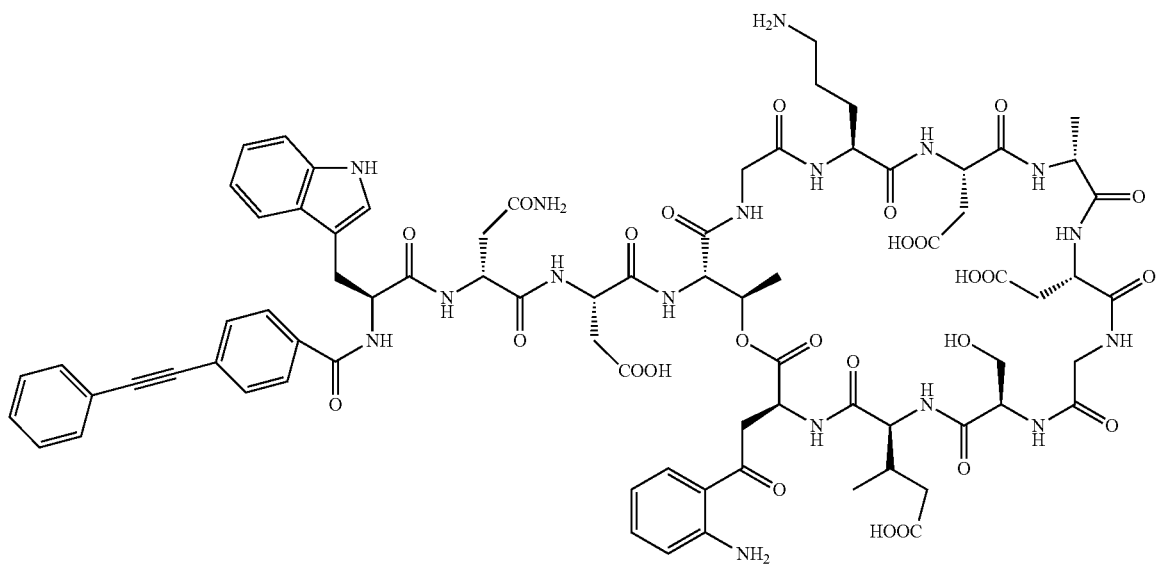

Example 6. Synthesis of Compound 6

Linear peptide resin-Gly-Asp(tBu)-DAla-Asp(tBu)-Orn(Boc)-Sar-Thr[O-Kyn-mGlu(tBu)-DSer(tBu)]-Asp(tBu)-DAsn(Trt)-Trp(Boc)-4-phenylethynyl-benzoyl was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the Sar/4-phenylethynyl-benzoyl-containing daptomycin analogues Compound 6. Cald. $[M+H]^+$ 1685.7, found $[M+H]^+$ 1685.6, $[M+2H]^{2+}$ 843.0.

Example 7. Synthesis of Compound 7

Linear peptide resin-Gly-Asp(tBu)-DAla-Asp(tBu)-Orn(Boc)-Gly-Thr[O-meKyn-mGlu(tBu)-DSer(tBu)]-Asp(tBu)-DAsn(Trt)-Trp(Boc)-(E)-3-(4-pentylphenyl) but-2-enoyl was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the methylated Kyn-containing daptomycin analogues Compound 7.

6

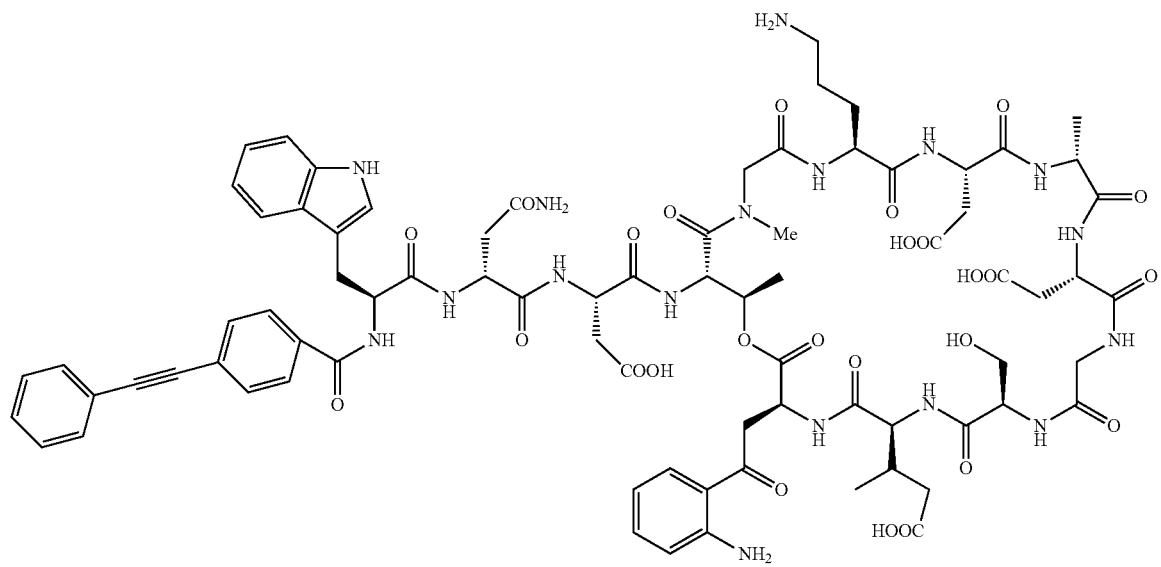

Compound 6

Compound 7

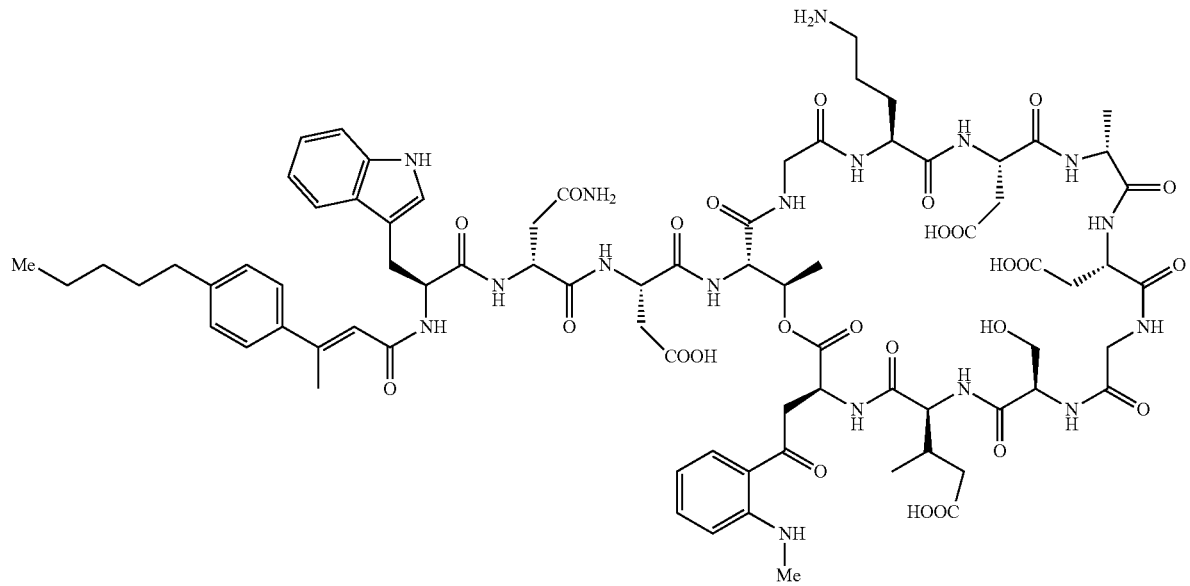

Example 8. Compound 1 Shows Better Antibacterial Activity than Daptomycin in a Neutropenic Mouse Thigh Infection Model Materials and Methods Biological assays were designed to compare the efficacies of compound 1 and compound 7 to daptomycin and other common antibiotics.

Compound 1 was tested against MRSA ATCC33591 in a neutropenic mouse thigh infection model. Both female and male ICR mice were rendered neutropenic by cyclophosphamide (three consecutive doses of 150 mg per kg delivered before infection). At day 4, bacteria were resuspended in sterile saline, 0.1 ml inoculum (MRSA ATCC33591, 5.0× $10^6$ c.f.u/ml) was injected into the left thighs of mice. At 2 h post-infection, mice received treatment with Compound 1 at 0.63, 1.25, 2.5, 5.0 mg per kg administered in a single dose (10 ml/kg), intravenous injection (five mice per group). At 24 h post-infection, the left thighs were aseptically removed, weighed, homogenized, serially diluted and plated on trypticase soy agar for c.f.u titres.

Results

From these in vivo studies, compound 1 showed significantly better antibacterial activity at doses of 1.25 and 2.50 mg/kg than daptomycin on mice with thigh infected with S. aureus. The results are illustrated in Table 1.

TABLE 1

Mouse thigh infection model (MRSA, ATCC 33591)

| drug | MIC (µg/ml) | Dose (mg/kg) | Thigh colony-forming units (c.f.u) (log(CFU/thigh), X ± SD, n = 5) | Δ |
|---|---|---|---|---|
| Control | | 0 | 8.90 ± 1.02 | |
| Compound 1# | 0.5 | 0.63 | 7.93 ± 0.85 | 0.97 |
| | | 1.25 | 7.13 ± 0.25** | 1.77 |

TABLE 1-continued

Mouse thigh infection model (MRSA, ATCC 33591)

| drug | MIC (µg/ml) | Dose (mg/kg) | Thigh colony-forming units (c.f.u) (log(CFU/thigh), X ± SD, n = 5) | Δ |
|---|---|---|---|---|
| | | 2.50 | 5.75 ± 0.35** | 3.15 |
| | | 5.00 | 3.72 ± 0.35** | 5.18 |
| daptomycin | 1 | 0.63 | 8.02 ± 0.48 | 0.88 |
| | | 1.25 | 7.81 ± 0.37* | 1.09 |
| | | 2.50 | 6.93 ± 0.57** | 1.97 |
| | | 5.00 | 3.93 ± 0.84** | 4.97 |

*controls versus all treatment groups, P < 0.05;
**controls versus all

Example 9. Compound 1 Decreases Infection of S. aureus in Right-Sided Endocarditis Rats Materials and Methods Male Sprague-Dawley rats (280-300 g) were intraperitoneally anesthetized with sodium pentobarbital solution (40 mg/kg). The rat chin area was treated with 75% alcohol. The right carotid artery was exposed through an anterior incision just slight right of midline above the calvicles. Polyethylene tubing was placed over 4-4.5 cm guided wire and passed within the right carotid artery into the left ventricle until resistance was met. Cardiac pulsations of the catheter indicated proper placement of the catheter tip at the apex of the heart. 0.5 ml inoculum of the overnight cultures (ATCC43300m 3.5×$10^4$ c.f.u./mL) was injected through a tail vein. After 24 hours of infection, the surviving rats were randomly divided into control group and treatment group. Compound 1 and daptomycin was administered via tail vein for 2 days (1 time/day). 24 h after the last administration, the animals were anesthetized and sacrificed. Vegetations and tissue samples were excised, weighed, homogenized, serially diluted and plated on trypticase soy agar for c.f.u titres.

Results

Compared with the control groups, the intraperitoneal injection of compound 1 could significantly decrease the infection of *S. aureus* in the right-sided endocarditis rats, which was also superior to daptomycin. The results are illustrated in Table 2.

TABLE 2

Right-sided endocarditis rat model (MRSA ATCC43300)

| | Dose (mg/kg) | No. of animals | Vegetation weight (g) | Log10 (CFU/g) of vegetation | Δ |
|---|---|---|---|---|---|
| Control | — | 3 | 0.029 ± 0.013 | 9.31 ± 0.84 | |
| Daptomycin | 40 | 3 | 0.007 ± 0.001** | 8.58 ± 0.55 | 0.73 |
| Compound 1 | 20 | 3 | 0.012 ± 0.002*** | 7.53 ± 1.08* | 1.78 |

*controls versus all treatment groups, P < 0.05;
**controls versus all treatment groups, P < 0.01;
***Compound 1 versus control p > 0.05

Example 10. Compounds 1 and 7 Shows Better In Vitro Antibacterial Activity than Daptomycin and Vancomycin Materials and Methods Anti-*Clostridium difficile* activity of compound 1 was tested on two strains, *C. difficile* BAA-1382 and ATCC3255, using the standard broth dilution method as described by the Clinical Laboratory Standard Institute.

Results

Both compound 1 and compound 7 showed the better activities than vancomycin and daptomycin. The results are illustrated in Table 3.

TABLE 3 in vitro anti-*Clostridium difficile* (MICs, µg/mL)

| | *Clostridium difficile* (µg/mL) | |
|---|---|---|
| | ATCCBAA-1382 | ATCC43255 |
| vancomycin | 1 | 1 |
| daptomycin | 1 | 1 |
| surotomycin | 0.5 | 0.5 |
| Compound 1 | 0.5 | 0.5 |
| Compound 7 | 0.25 | 0.25 |

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:
1. A compound having a Formula VII:

(VII)

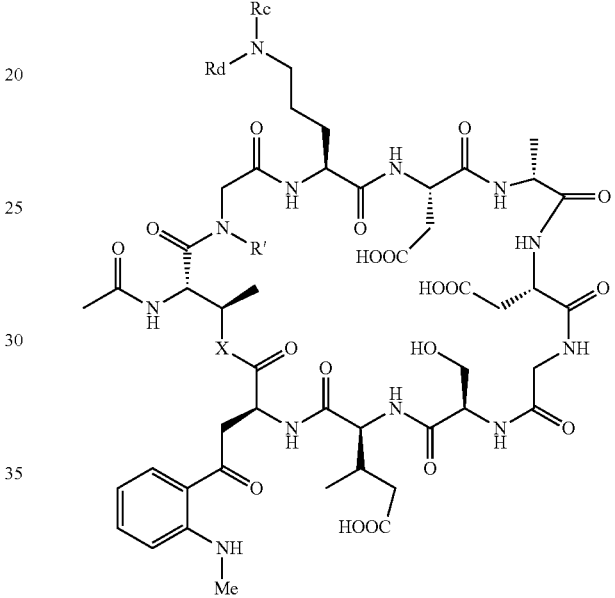

Formula VII wherein,
(i) R is substituted alkenyl, unsubstituted alkenyl, substituted alkynyl, or unsubstituted alkynyl, or
(ii) R is substituted $C_5$-$C_{14}$ alkyl or unsubstituted $C_5$-$C_{14}$ alkyl,
R', Rb, Rc, and Rd are independently hydrogen, substituted alkyl, or unsubstituted alkyl, and
X is O or NRa, where Ra is hydrogen, unsubstituted alkyl, substituted alkyl, substituted alkenyl, unsubstituted alkenyl, substituted alkynyl, unsubstituted alkynyl, substituted polyheteroayl, unsubstituted polyheteroryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl.

2. The compound of claim 1, wherein X is O or NH.
3. The compound of claim 1, wherein:
Ra is H, or methyl;
R' is H or methyl or ethyl;
Rc and Rd are independently H, or methyl;
X is O or NH; and R is unsubstituted $C_5$-$C_{14}$ alkyl, substituted $C_5$-$C_{14}$ alkyl, unsubstituted $C_5$-$C_{14}$ alkenyl, substituted $C_5$-$C_{14}$ alkenyl, unsubstituted $C_5$-$C_{14}$ alkynyl, substituted $C_5$-$C_{14}$ alkynyl, unsubstituted $C_5$-$C_{14}$ aryl, substituted $C_5$-$C_{14}$ aryl, unsubstituted $C_5$-$C_{14}$ polyaryl, substituted $C_5$-$C_{14}$ polyaryl, unsubstituted $C_5$-$C_{14}$ polyheteroaryl, or substituted $C_5$-$C_{14}$ polyheteroaryl.

4. The compound of claim 1, having the formula:

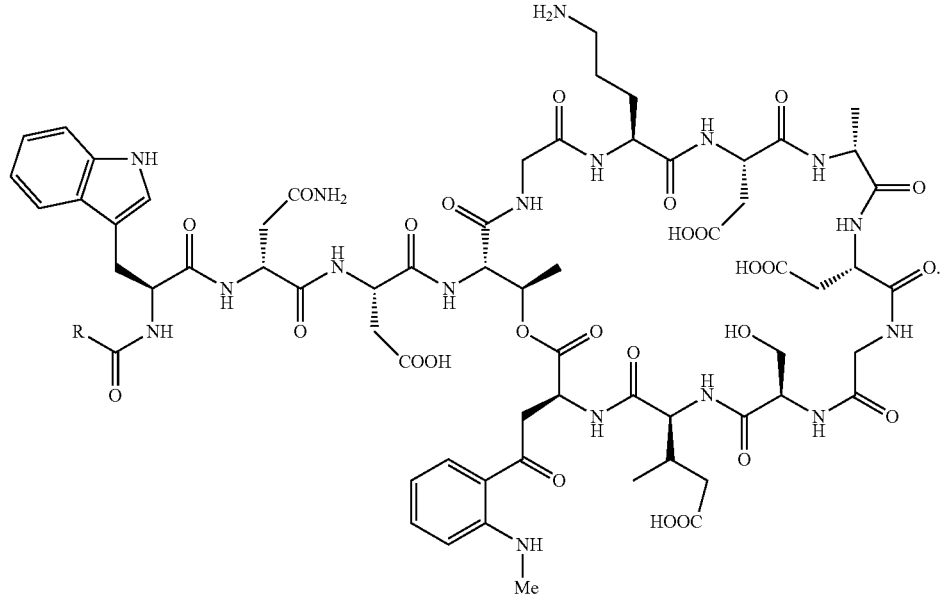

Formula VIII

5. A compound having a structure:

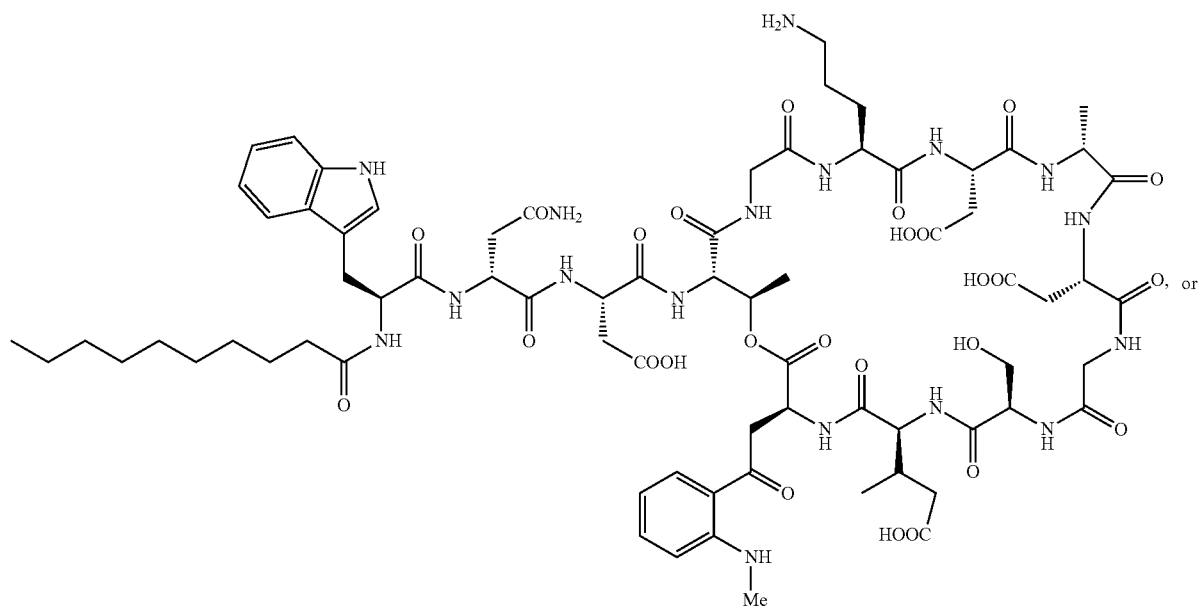

, or

-continued
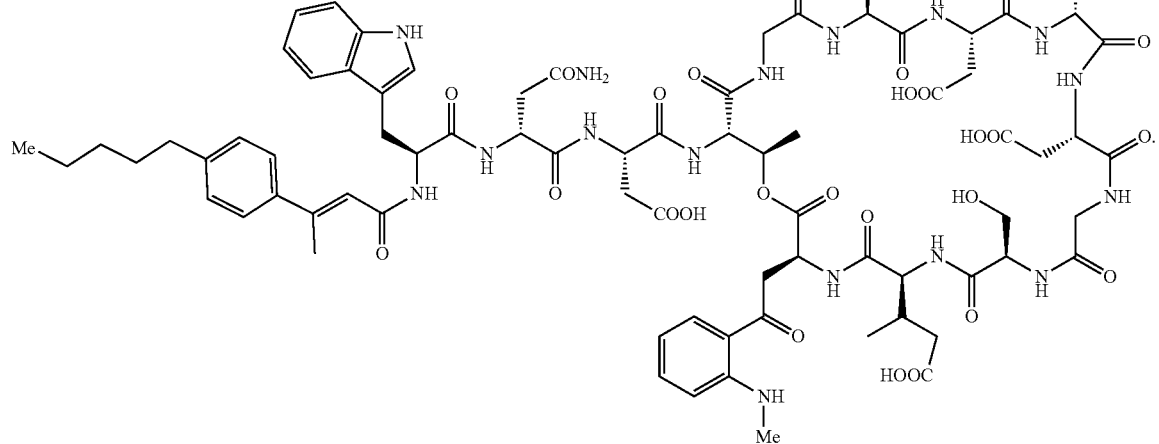
7
6. A pharmaceutical composition comprising the compound of claim 1.
7. The compound of claim 5 having the structure of compound 7:
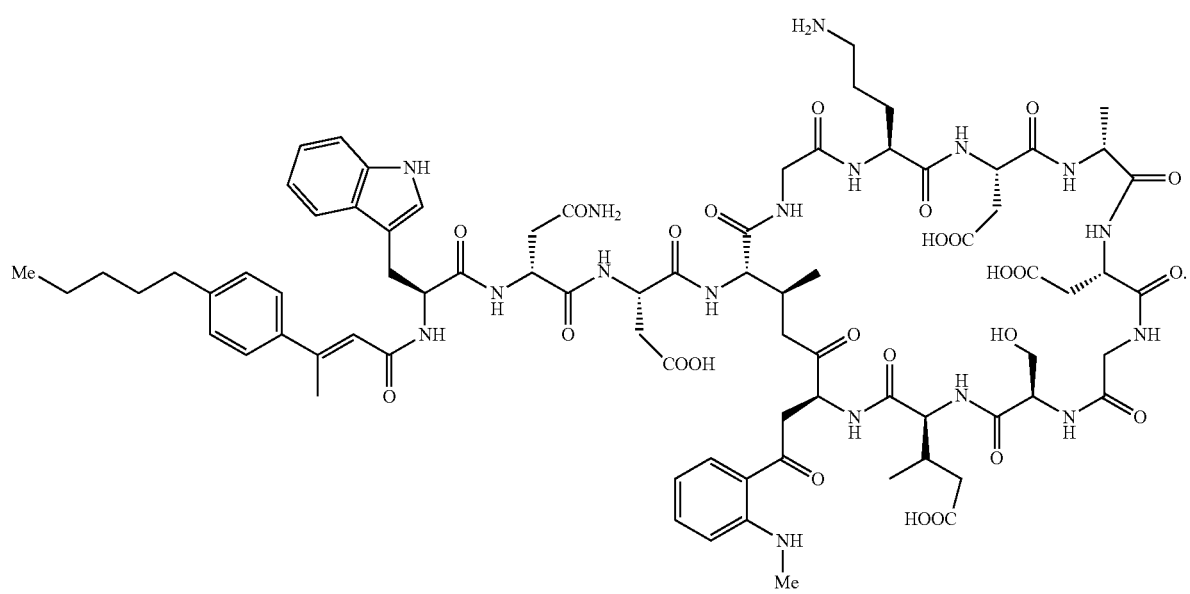
7
8. The compound of claim 4, wherein R is $C_9H_{19}$ or (E)-2-(4-pentylphenyl) propenyl.
* * * * *